US011963813B2

(12) United States Patent
Nehmeh et al.

(10) Patent No.: US 11,963,813 B2
(45) Date of Patent: Apr. 23, 2024

(54) POSITRON EMISSION TOMOGRAPHY SYSTEM WITH ADAPTIVE FIELD OF VIEW

(71) Applicant: CORNELL UNIVERSITY, Ithaca, NY (US)

(72) Inventors: Sadek Nehmeh, Oakland Gardens, NY (US); Nikolaos A. Karakatsanis, Astoria, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 234 days.

(21) Appl. No.: 17/413,376

(22) PCT Filed: Dec. 12, 2019

(86) PCT No.: PCT/US2019/066047
§ 371 (c)(1),
(2) Date: Jun. 11, 2021

(87) PCT Pub. No.: WO2020/123846
PCT Pub. Date: Jun. 18, 2020

(65) Prior Publication Data
US 2022/0022834 A1 Jan. 27, 2022

Related U.S. Application Data

(60) Provisional application No. 62/779,225, filed on Dec. 13, 2018.

(51) Int. Cl.
A61B 6/00 (2006.01)
A61B 6/03 (2006.01)
(Continued)

(52) U.S. Cl.
CPC ............... *A61B 6/54* (2013.01); *A61B 6/037* (2013.01); *A61B 6/4266* (2013.01); *G01T 1/2018* (2013.01); *G01T 1/202* (2013.01)

(58) Field of Classification Search
CPC ............................. G01T 1/2018; G01T 1/202
See application file for complete search history.

(56) References Cited

U.S. PATENT DOCUMENTS 8,594,404 B2    11/2013  Yamaya et al.
2005/0109943 A1  5/2005  Vaquero et al.
(Continued)

FOREIGN PATENT DOCUMENTS

JP      H09-211130 A     8/1997
WO   WO-2005/029507 A2   3/2005
(Continued)

OTHER PUBLICATIONS

EP Extended Search in EP 19897281.2, Report dated Jun. 17, 2022.
(Continued)

*Primary Examiner* — Blake C Riddick
(74) *Attorney, Agent, or Firm* — FOLEY & LARDNER LLP

(57) ABSTRACT

A PET imaging system, with parallel detector rings sharing a common axis (e.g., rings with one or more detector elements in the axial direction and two or more detector elements in the transaxial direction), may have an adaptive axial and/or transaxial FOV by employing a sparse detector configuration and adapting the size of axial gaps between rings and/or the size of transaxial gaps between detector elements in each ring. The axial FOV may be dynamic, enabling PET data acquisition in multiple modes (e.g., "retracted" with detector rings in a compact configuration, and "extended" with detector rings extended for longer axial FOV). The transaxial FOV may be dynamic, enabling an adaptive detector ring diameter for different body part contours. The sparse detector ring configurations may be used to extend the scanner axial and/or transaxial FOV, or (Continued)

retain the current system's FOV with half the number of (or otherwise fewer) detector elements.

26 Claims, 16 Drawing Sheets

(51) Int. Cl.
*A61B 6/42* (2024.01)
*G01T 1/20* (2006.01)
*G01T 1/202* (2006.01)

(56) References Cited

U.S. PATENT DOCUMENTS

| | | | | |
|---|---|---|---|---|
| 2008/0033279 | A1* | 2/2008 | Ladebeck | G01R 33/481 250/363.03 |
| 2008/0107229 | A1* | 5/2008 | Thomas | A61B 6/037 378/207 |
| 2008/0111081 | A1* | 5/2008 | Chuang | G01T 1/1603 250/363.03 |
| 2008/0173819 | A1* | 7/2008 | Grazioso | G01T 1/2985 250/363.05 |
| 2009/0072155 | A1* | 3/2009 | Watson | A61B 6/037 250/363.03 |
| 2010/0040197 | A1* | 2/2010 | Maniawski | G01T 1/2985 378/65 |
| 2011/0092814 | A1 | 4/2011 | Yamaya et al. | |
| 2011/0150306 | A1* | 6/2011 | Ross | G01T 1/1611 250/363.04 |
| 2012/0104263 | A1* | 5/2012 | Gagnon | G01T 1/1644 250/336.1 |
| 2012/0267536 | A1* | 10/2012 | Gagnon | G01T 1/1644 250/363.03 |
| 2012/0271164 | A1* | 10/2012 | Gagnon | A61B 6/037 600/427 |
| 2013/0237818 | A1 | 9/2013 | Herrmann | |
| 2014/0316258 | A1 | 10/2014 | Hahn et al. | |
| 2015/0065869 | A1* | 3/2015 | Daghighian | A61B 6/5258 600/425 |
| 2016/0183893 | A1* | 6/2016 | Zhang | A61B 6/0407 250/363.05 |
| 2017/0038485 | A1 | 2/2017 | McGowan et al. | |
| 2017/0311919 | A1* | 11/2017 | Gagnon | A61B 6/482 |
| 2018/0136344 | A1 | 5/2018 | Nelson et al. | |
| 2018/0350078 | A1* | 12/2018 | Sun | G06T 7/11 |
| 2020/0345322 | A1* | 11/2020 | Bai | A61B 6/4266 |
| 2021/0030387 | A1* | 2/2021 | Andreyev | A61B 6/5282 |

FOREIGN PATENT DOCUMENTS

| | | |
|---|---|---|
| WO | WO-2015/019312 | 2/2015 |
| WO | WO-2019/106150 A1 | 6/2019 |

OTHER PUBLICATIONS

Karakatsanis Nicolas A et al: "Evaluation of Image Quality and Quantitation in a Clinical PET Scanner with a Uniformly Sparse Detector Rings Configuration", 2018 IEEE Nuclear Science Symposium and Medical Imaging Conference Proceedings (NSS/MIC), IEEE, Nov. 10, 2018 (Nov. 10, 2018), pp. 1-9.
International Preliminary Report on Patentability on PCT/US2019/066047 dated Jun. 24, 2021.
International Search Report and Written Opinion on PCT PCT/US2019/066047 dated Apr. 21, 2020.

* cited by examiner

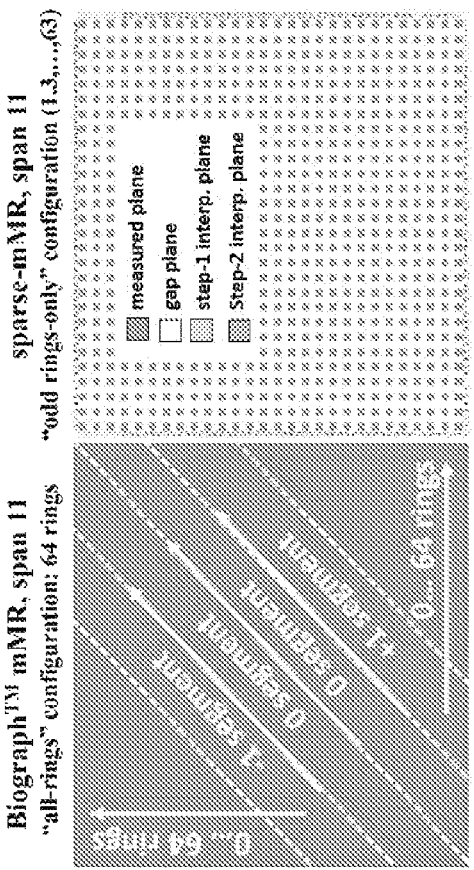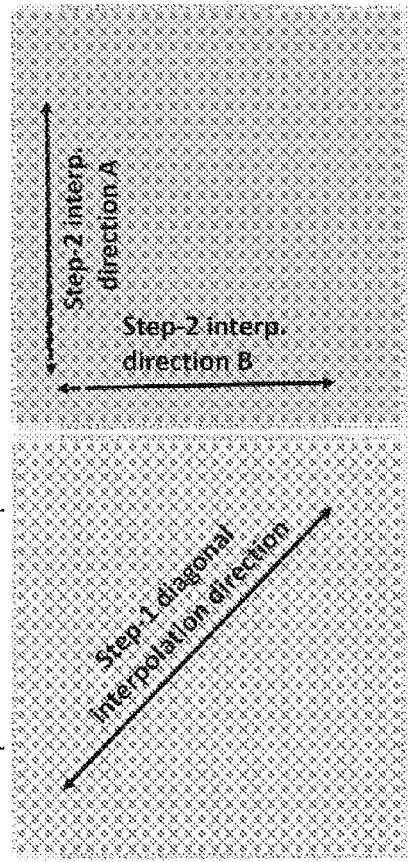
FIG. 4A FIG. 4B FIG. 4C FIG. 4D

POSITRON EMISSION TOMOGRAPHY SYSTEM WITH ADAPTIVE FIELD OF VIEW

CROSS REFERENCE TO RELATED APPLICATION

This application is a U.S. National Phase under 35 U.S.C. § 371 of International Application No. PCT/US2019/066047, filed on Dec. 12, 2019, which claims priority to U.S. Provisional Patent Application No. 62/779,225 entitled "EXTENDED AXIAL FIELD OF VIEW PET WITH SPARSE RINGS," filed Dec. 13, 2018, and incorporated herein by reference in their entireties.

BACKGROUND OF THE DISCLOSURE

Positron emission tomography (PET) is an imaging modality for translational medicine that can offer highly specific and sensitive tomographic imaging of molecular interactions and pathways in humans. PET is widely used in oncology, neurology, and cardiology, with more than 2,500 PET/CT scanners currently operational in the USA, and the number of clinical PET studies exceeding two million per year.

SUMMARY OF THE DISCLOSURE

Various embodiments of the disclosure relate to a positron emission tomography (PET) imaging system. The imaging system may comprise a controller having a processor and a memory with instructions executable by the processor to control scanning of subjects. The system may comprise a PET scanner having a set of detector structures. The detector structures may be detector rings. The PET scanner may be an axially-sparse PET scanner. The detector structures may be parallel. The detector structures may share a common axis. Each detector structure may have one or more radiation detector elements. A detector element may be an individual detector, an array of individual detectors (detector block) or an array of detector blocks (detector module). Each detector structure may have a corresponding axial width. The detector structures may be spaced apart from each other along the axis to define gaps between detector structures in the set of detector structures such that an axial field-of-view (FOV) of the PET imaging system is greater than a sum of the corresponding axial widths of the detector structures.

In one or more embodiments, each detector structure in the PET scanner may comprise a same number of detector elements in an axial direction. In one or more embodiments, detector structures in the PET scanner may comprise a variable number of detector elements in an axial direction. In one or more embodiments, a first detector structure of the set of detector structures in the PET scanner may comprise a first number of detector elements in an axial direction and a second detector structure of the set of detector structures in the PET scanner may comprise a second number of detector elements in the axial direction.

In one or more embodiments, each detector element in the PET scanner may have a same set of dimensions. In one or more embodiments, a first subset of detector elements in the PET scanner may have a first set of dimensions and a second subset of detector elements in the PET scanner may have a second set of dimensions different from the first set of dimensions. Each detector element in the second subset may be different from any of the detector elements in the first subset.

In one or more embodiments, gaps between detector structures may be uniform in the PET scanner. In one or more embodiments, gaps between detector structures may be variable in the PET scanner. In one or more embodiments, gaps between detector structures may be position-dependent such that axial gaps differ at different positions in the set of detector structures.

In one or more embodiments, each detector element in the PET scanner may have a same orientation. In one or more embodiments, orientations of detector elements in the PET scanner may vary such that a first subset of detector elements in the PET scanner may have a first orientation and a second subset of detector elements in the PET scanner may have a second orientation different from the first orientation. Each detector element in the second subset may be different from any of the detector elements in the first subset.

In one or more embodiments, the PET imaging system may comprise a scanner drive mechanism configured to adjust gaps between detector structures in the set of detector structures so as to adjust the axial FOV of the PET imaging system.

In one or more embodiments, the controller may be configured to determine spacing between detector structures based on a criterion. The controller may be configured to control the scanner drive mechanism to adjust gaps between detector structures to correspond with the determined spacing. The controller may be configured to perform a scan with the PET scanner following adjustment of gaps.

In one or more embodiments, the controller may be configured to perform a scan with the PET scanner and use the scanner drive mechanism to dynamically adjust gaps between detector structures during the scan.

In one or more embodiments, the controller may be configured to perform a first scan using the PET scanner with a first set of gaps between detector structures. The controller may be configured to determine a second set of gaps based on the first scan. The controller may be configured to control the scanner drive mechanism to adjust gaps between detector structures to correspond with the second set of gaps. The controller may be configured to perform a second scan following adjustment of gaps.

In one or more embodiments, the controller may be configured to control the scanner drive mechanism to adjust gaps based on a size of a subject to be scanned.

In one or more embodiments, detector elements in each detector structure may be spaced uniformly in a transaxial plane. In one or more embodiments, detector elements in each detector structure may be spaced non-uniformly in a transaxial plane.

In one or more embodiments, the PET scanner comprises gaps in both transaxial and axial directions. The gaps may be uniform or non-uniform in the transaxial direction, and/or the gaps may be uniform or non-uniform in the axial direction. The gaps may be position dependent within the scanner gantry. For example, the PET scanner may comprise transaxial gaps in one part (e.g., a first segment of the gantry), and axial gaps in another part (e.g., a second segment of the gantry).

In one or more embodiments, the controller may be configured to apply an axial projection interpolation model to infer measurements missing due to gaps between detector structures.

In one or more embodiments, the controller may be configured to apply a component-based normalization model to PET scan data before three-dimensional PET image reconstruction.

In one or more embodiments, gaps may be uniformly distributed. The gaps may separate detector structures by distances substantially equal to axial widths of the detector structures.

In one or more embodiments, the controller may be configured to scan subjects via continuous bed motion (CBM) acquisition of PET data to compensate for data missing due to gaps between detector structures.

In one or more embodiments, the axial FOV of the PET imaging system may be substantially twice as great as a compact-structure configuration in which there are no gaps between detector structures.

In one or more embodiments, the axial FOV of the PET imaging system may be multi-fold larger than in the compact-structure configuration (e.g., any multiple of two or greater, such as more than twice as large, at least 2.5 times as large, or at least three times as large).

In one or more embodiments, axial and/or transaxial gaps may be arranged such that N number of detectors may be interleaved, with uniform or non-uniform physical gaps. In certain embodiments, a width of physical gaps may be equal to an axial length of the N-detector elements. In certain embodiments, the width of physical gaps is not equal to the axial length of the N-detector elements.

In one or more embodiments, the controller may be configured to rotate a gantry during scanning to compensate for data missing due to gaps between detector structures. The gantry may be rotated via a gantry drive mechanism.

Various embodiments of the disclosure relate to a PET imaging system comprising a plurality of detector structures. Each detector structure may comprise one or more PET detector elements. The PET imaging system may comprise a scanner drive mechanism coupled to the plurality of detector structures. The scanner drive mechanism may be configured to drive the plurality of detector structures axially between a retracted configuration and an expanded configuration. The plurality of detector structures may be closer to each other in the retracted configuration than in the expanded configuration. In the expanded configuration, an axial field-of-view (FOV) of the PET imaging system may be greater than in the retracted configuration.

In one or more embodiments, the scanner drive mechanism may comprise one or more mechanical components for physically moving one or more of the detector structures.

In one or more embodiments, the one or more mechanical components may move detector structures independently of each other. In one or more embodiments, the one or more mechanical components may move two or more detector structures in unison.

In one or more embodiments, the one or more mechanical components comprise one or more gears, wheels, axels, motors, springs, and/or magnetic elements. In one or more embodiments, each detector structure may be driven by its own mechanism. In one or more embodiments, each detector structure may be driven independently. In one or more embodiments, the scanner drive mechanism may comprise mechanical components that function as one or more scissor lifts.

In one or more embodiments, the PET imaging system may comprise a controller configured to control the scanner drive mechanism to drive the plurality of detector structures between the retracted configuration and the expanded configuration.

In one or more embodiments, the controller may be configured to drive the plurality of detector structures in real time so as to change gaps between detector structures during a scan of a subject.

Various embodiments of the disclosure relate to a method of performing PET scanning of a subject using a PET imaging system. The PET imaging system may have a PET scanner. The PET scanner may have a set of detector structures that share a common axis. The set of detector structures may be axially spaced apart from each other so as to define gaps between detector structures. The method may comprise performing a first scan of a subject to capture a first PET dataset with a first axial field-of-view (FOV). The first scan may be performed via a controller of the PET imaging system. The set of detector structures may be separated from each other by a first set of gaps between detector structures. The method may comprise determining a second set of gaps between detector structures corresponding to a second axial FOV different from the first axial FOV. The second set of gaps may be determined via the controller. The second set of gaps may be determined based on the PET dataset. The method may comprise applying the second set of gaps to the set of detector structures to change distances between detector structures. The second set of gaps may be applied via the controller. The method may comprise performing a second scan of the subject to capture a second PET dataset with a second axial FOV. The second scan may be performed via the controller.

In one or more embodiments, the method may comprise applying an axial projection interpolation model to infer measurements missing due to gaps between detector structures. The axial projection interpolation model may be applied via the controller.

In one or more embodiments, the method may comprise rotating a gantry during scanning to compensate for data missing due to gaps between detector structures. The gantry may be rotated via the controller.

In one or more embodiments, the method may comprise continuous bed motion (CBM) during scanning to compensate for data missing due to gaps between detector structures. CBM may be implemented via the controller.

In various embodiments, the method may comprise continuous bed motion (CBM) and/or gantry rotation to compensate for missing data due to gaps. CBM and/or gantry rotation may be implemented during scanning via the controller.

In various embodiments, a sparse detector ring configuration may be incorporated into pre-clinical PET imaging.

In various embodiments, axial FOV may be dynamically adjusted to accommodate subjects of different lengths. For example, axial FOV may be extended by increasing gaps to allow imaging of taller subjects, or contracted by decreasing gaps for shorter subjects.

In various embodiments, the PET imaging system may have a dynamic PET scanner diameter that may be adjustable for different subjects. For example, transaxial FOV may be extended to accommodate larger animal diameters, and transaxial FOV may be retracted to accommodate smaller animal diameters. In certain embodiments, PET scanner diameter may be dynamically adjusted by, for example, mechanically translating detector elements radially.

In various embodiments, a PET scanner may comprise detector elements that are transaxially sparse (e.g., expanded or spaced apart). Transaxial sparsity may be in addition to, or in place of, axial sparsity. In one or more embodiments, a PET gantry may be rotatable to compensate for data missing due to transaxial gaps between detector elements.

In various embodiments, the controller may be configured to apply sparse data reconstruction models, machine learning models, deep learning models, and/or other artificial intelligence models to compensate for loss of counts due to gaps between detector structures.

Various embodiments of the disclosure relate to a positron emission tomography (PET) imaging system comprising a plurality of detector structures. Each detector structure may comprise one or more PET detector elements. The PET imaging system may comprise a scanner drive mechanism. The scanner drive mechanism may be coupled to the plurality of detector elements. The scanner drive mechanism may be configured to drive the plurality of detector elements. The scanner drive mechanism may be configured to drive the plurality of detector elements transaxially. The scanner drive mechanism may be configured to drive the plurality of detector elements transaxially between a retracted configuration and an expanded configuration. In the expanded configuration, a transaxial axial field-of-view (FOV) of the PET imaging system may be greater than in the retracted configuration.

In various embodiments, the scanner drive mechanism may comprise one or more mechanical components. The mechanical components may be configured to radially move one or more of the detector elements.

In various embodiments, detector structures share a common axis. Each detector structure may have a corresponding axial width. The detector structures may be spaced apart from each other along the axis to define gaps between detector structures in the set of detector structures. The detector structures may be spaced apart such that an axial FOV of the PET imaging system is greater than a sum of the corresponding axial widths of the detector structures.

Various embodiments of the disclosure relate to a positron emission tomography (PET) imaging system comprising a controller having a processor and a memory with instructions executable by the processor to control scanning of subjects. The PET imaging system may comprise a PET scanner having a set of detector structures. The detector structures may share a common axis. Each detector structure may have one or more radiation detector elements. The detector elements may be configured to be radially translatable. The detector elements may be configured to be radially translatable such that a transaxial field-of-view (FOV) of the PET imaging system is adjustable. The transaxial FOV of the PET imaging system may be dynamically adjustable during scanning of subjects.

In various embodiments, each detector structure may have a corresponding axial width. Detector structures may be spaced apart from each other along the axis to define gaps between detector structures in the set of detector structures. The detector structures may be spaced apart such that an axial FOV of the PET imaging system is greater than a sum of the corresponding axial widths of the detector structures.

In various embodiments, the imaging system may comprise a scanner drive mechanism. The scanner drive mechanism may be coupled to the controller. The controller may be configured to use the drive mechanism during scanning. The scanner drive mechanism may be coupled to one or more mechanical components capable of moving detector structures and/or capable of moving detector elements. The controller may be configured to change transaxial FOV by radially translating one or more detector elements, and/or the controller may be configured to change axial FOV by adjusting gaps between detector structures.

Various embodiments of the disclosure relate to a PET imaging system with a parallel set of detector rings sharing a common axis (e.g., rings comprising of one or more detector elements in the axial direction and of two or more detector elements in the transaxial direction). The PET imaging system may have an adaptive axial and/or transaxial FOV by employing a sparse detector configuration and adapting the size of the axial gaps between the rings and/or the size of the transaxial gaps between the detector elements in each ring. The axial FOV may be dynamic, enabling PET data acquisition in multiple modes. For example, in a "retracted mode," detector rings may be in a compact configuration to maximize sensitivity per PET transaxial slice, and in an "extended mode" (e.g., a sparse-ring configuration) detector rings may be extended for applications needing longer axial FOV, such as compartmental kinetic analysis (CKA), simultaneous multi-system organ imaging, and pediatric PET imaging. The transaxial FOV may be dynamic, enabling the system to adapt the detector ring diameter for different body part contours. The sparse detector ring configurations may be used to extend the scanner axial and/or transaxial FOV, or retain the current system's FOV yet with half the number of (or otherwise fewer) detector elements.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIGS. 4A-4D depict fully-3D PET sinograms (Michelogram format) illustrating, for "all-rings" and "odd-rings-only" configurations of FIGS. 3A and 3B, respectively, the measured "non-empty" (dark blue), missed "empty" (white) and interpolation inferred sinogram planes after step-1 (light blue) and step-2 (gray) of the interpolation process, according to potential embodiments. It is noted that, in step-1, interpolation occurs only across the indicated diagonal direction in the Michelogram and accepts as input only pairs of planes with measured counts. In step-2, interpolation occurs along either the rows (direction A) or the columns (direction B) of the Michelogram and involves pair of planes that include both measured and interpolated counts.

FIG. 10D illustrates and example sparse configuration.

FIGS. 13B, 13D show the coronal view through the center of the smallest sphere (10 mm diameter). FIG. 13B shows increased level of noise at the edges, whereas in image FIG. 13D levels of noise at the edges are less elevated.

DETAILED DESCRIPTION

Figure 1:
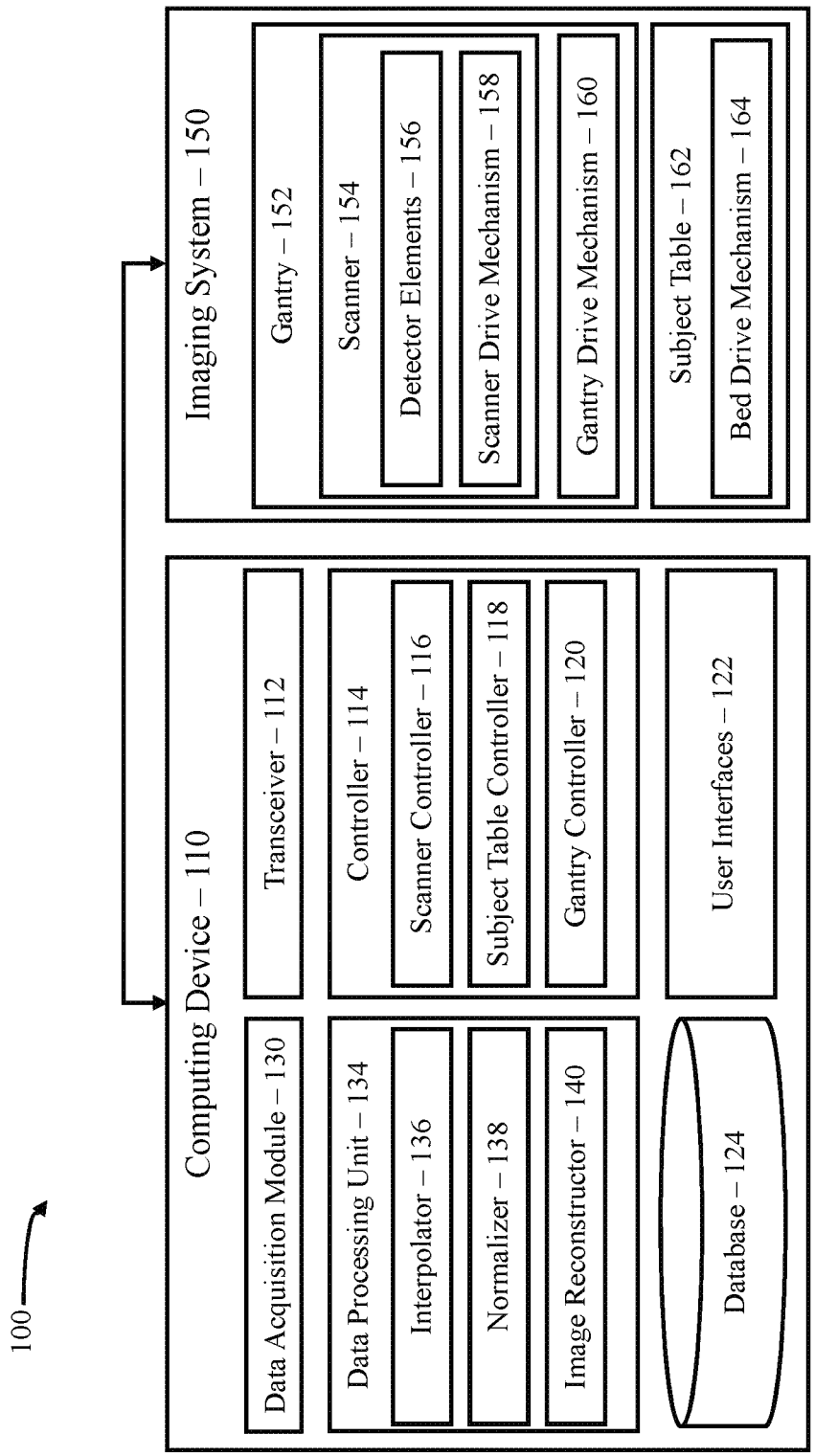
FIG. 1 depicts an example system capable of implementing disclosed approaches for PET scanning using sparse ring detector configurations, according to potential embodiments.

The various concepts introduced above and discussed in greater detail below may be implemented in any of numerous ways, as the described concepts are not limited to any particular manner of implementation. Examples of specific implementations and applications are provided primarily for illustrative purposes.

PET scanners use a set of compact rings of scintillating crystals to detect the 511 keV gammas annihilating from positrons emitted by a radiotracer intravenously injected in the patient to target specific disease pathways. The role of PET imaging can be limited to the imaging of one single organ at a time due to its short axial field-of-view (FOV), which can be less than 22 cm. A whole-body PET scan thus requires the reconstruction of serial scans along the body of the patient at multiple axial position. Due to its short axial FOV, the role of PET imaging may not be fully exploited. For example, it can be difficult to use PET imaging in multi-system organs such as brain-heart interactions, brain-guts interactions, and heart-guts interactions. Moreover, the clinical implementation of compartmental kinetic analysis (CKA) of dynamic PET images, which was shown to have higher prognostic and predictive values than static semi-quantitative Standard Uptake Value (SUV) measurements, has also been constrained by a number of factors. For example, the dynamic PET imaging can be possible for only one single organ position at a time, and there is a lack of availability of accurate input function (IF) measurements.

In various embodiments, a PET imaging system has a dynamic axial FOV that enables acquiring PET data in a plurality of modes. In a first mode, the "retracted mode," the rings are in a compact configuration to achieve maximum sensitivity per PET transaxial slice. In a second mode, the "extended mode" (which can also be referred to as the sparse ring configuration), the rings are extended for applications needing longer axial FOV, such as CKA (including whole body CKA), simultaneous multi-system organ imaging, and pediatric PET imaging.

The example sparse-rings PET scanner of embodiments of the present disclosure enables increases in (e.g., doubling of) the axial FOV of a standard PET scanner without the costs that would be required for detector rings with compact configurations. Similarly, the disclosed sparse-rings PET scanner allows for the axial FOV of standard PET scanners but using half the number of detector rings, thus reducing the cost, which makes it feasible particularly for developing countries where patient demand is high while funding is limited.

The PET scanner may include gamma photon detectors of any suitable configuration. The PET scanner of the present disclosure can include a set of independent gamma photon detector rings controlled by a mechanical system that enable the rings' extension and retraction along an axial direction.

The PET scanner of the present disclosure can have a dynamic axial FOV that varies in different scanners. The axial FOV can have a range that extends to any suitable axial length depending on the particular scanner application. Each detector block can include a number of gamma photon detector crystals in the axial direction. The PET scanner can include a gap of a predetermined length (W) to maintain comparable performance between the sparse ring and compact PET systems.

The system can include a mechanical system to extend and retract the block detector rings. In some implementations, the mechanical system can include a scissor lift mechanism that can be driven by stepper motor to extend and retract the detector block rings.

The PET scanner of the present disclosure can be used in a number of research and medical conditions. For example, the PET scanner can be used in compartment kinetic modeling (CKM). CKM of dynamic PET images is a complex approach. Previously, one of the limitations of CKM is the measurement input function (IF), which may be deduced by drawing arterial blood or by deriving it from the dynamic PET images using a region of interest drawn over the heart left ventricle or the artery (problematic due to partial volume effect). However, imaging the heart was limited because of the short FOV of a traditional PET scanner that could not also capture the heart in the image. The PET scanner of the present disclosure has an increased axial scan length to ensure the heart or the aorta are always included within the axial FOV. With a dynamic axial FOV it becomes plausible in studies that focus on the brain or the thorax to extend the FOV during the first few minutes post-radiotracer injection to include the heart or the aorta in order to deduce the input function. In some implementations, later, the FOV can be retracted (after the input function decays) to focus over the organ of interest to increase the sensitivity per PET transaxial plane. This can improve the corresponding signal-to-noise ratio.

The PET scanner of the present disclosure can also be used in whole body full compartmental kinetic analysis (CKA). For example, the CKA of dynamic PET images can provide quantitative parameters that more closely relate to the underlying pathology than semi-quantitative indices, such as the Standard Uptake Value, SUV (deduced from static PET images), as well as higher tumor contrast. However, due to the limited axial FOV of current PET scanners, PET whole body CKA with PET is not feasible. With the capability to extend the axial FOV, the PET scanner of the present disclosure can provide a solution to perform whole body CKA of dynamic PET data at limited cost.

The PET scanner of the present disclosure can be used in multi-system disease imaging. The diagnostic and therapeutic pathways usually concentrate on single organ pathology or dysfunction. However, there are increasing evidence showing that an organ condition can be a part of multisystem web of concurrent or contemporaneous abnormalities involving abnormal metabolism, hematopoietic cell activation, and inflammation. Furthermore, many distant organs often interface together consistently as a team to orchestrate a disease process and dysfunction in "One Axis" that resonates across the network as a multisystem response. Understanding such system-based interactions is a new frontier in medicine and requires a broad-based approach to the disease if we are to better design futuristic therapeutic interventions. For example, the "Heart-Brain Axis" is a multi-system on which the PET scanner of the present disclosure can be used.

A complex interaction exists between the nervous and cardiovascular systems. From a clinical perspective, the heart-brain axis can be approached as (a) the effects of cardiovascular disease on the nervous system (such as cardioembolic strokes in atrial fibrillation, or (b) the effects of neurological disorders on the cardiovascular system (such as stress cardiomyopathy after aneurysmal subarachnoid hemorrhage and stroke.

Embodiments of the PET scanner the PET scanner of the present disclosure can be used to image cardiovascular disease initiating in brain Disease. The effect of cardiovascular disease can be indirect on the brain such in the case of Alzheimer's disease as a result of a reduction in the amount of oxygen in the brain, which can set off a cascade of events, including hypoxia, that trigger Alzheimer's disease (brain hypoxia initiates overexpression of BACE1, a gene involved in the production of Amyloid-beta plaques found in the brains of Alzheimer's patients). Acute myocardial infarction leads to an early inflammatory response, which stimulates adverse left ventricular remodeling and triggers brain microglia activation in a biphasic pattern.

Embodiments of the PET scanner of the present disclosure can be used to monitor mental stress and cardiovascular disease. In the last 50 years, the role of the autonomic nervous system in the development and progression of heart disease and failure has been studied extensively. Emotional stress specifically rage, anxiety and depression are considered as both triggers and predisposing causes of angina pectoris. Depression and anxiety are also associated with worse outcome of coronary artery disease (CAD), including higher mortality and more frequent ventricular dysrhythmias. Several studies have also shown that the distressed personality can be considered as a risk marker for poor health outcomes in patients with cardiovascular disease, including CAD. The pathway through which distressed personality induces cardiac disorders is ambiguous, especially that it may induce myocardial ischemia even in patients with no history of CAD. As a result, there is growing interest in investigating different forms of mental stress.

An understanding of the interaction between the heart and the brain that can be provided by the PET scanner of the present disclosure can impact more than 5 million Americans suffering from Alzheimer's Disease and more than 17 million people who die annually from cardiovascular disease. A systems-based, multi-organ molecular imaging strategy, like in the case of the case of the Heart-Brain Axis, may assist in the development of targeted anti-inflammatory therapies that may benefit both systems by providing risk assessment, identifying therapeutic target expression, and monitoring intervention effectiveness. Other applications that may benefit from multi-system imaging shall also include anxiety, depression, metabolic syndrome and endocrine homeostasis, and neurodegenerative diseases. For these complex conditions, the simultaneous study of multiple body organs would advance our understanding of pathophysiology and spur translation of basic research.

PET scanners can include multiple rings of scintillating detectors that can be set tightly together. Such PET scanners may have a limited axial FOV. To extend the axial FOV, the PET scanner could include additional detector rings, but may be cost prohibitive. Example embodiments of the PET scanner of the present disclosure have an increased axial FOV by including sparse detector rings or sparse multi-detector rings with gaps every N detector rings. This can increase (e.g., double or more) the corresponding axial FOV while maintaining the system sensitivity. Additionally, the PET scanner of the present disclosure can maintain the same cost as the standard, commercial PET scanners.

The present disclosure describes example embodiments of PET scanners with dynamic axial FOVs. The PET scanner can acquire PET data with an extended axial FOV by dynamically, and in real time, extending the axial FOV (e.g., by double or more) by using a sparse detector rings configuration. Additionally, the PET scanner can act in retracted axial FOV to increase the sensitivity per transaxial position. In some implementations, the PET scanner can extend to one meter or more to image multi-organ systems, such as those in the brain and the torso.

In some implementations, the PET scanner can reduce the scanning time of a PET scan. The sparse ring configuration can enable reducing the scan time by ~50% in a whole-body PET scan and doubling the axial FOV while maintaining the overall system sensitivity. The PET scanner can improve patients' comfort by reducing the scan time (in particular, in claustrophobic subjects and pediatric patients where patient motion during the scan can be reduced by minimized the scan time).

In some implementations, the PET scanner can provide greater throughput. The reduction in the scan time due to the larger coverage per PET axial FOV can also increase patient throughput, a major consideration in places where patient demand is high while space restrictions prevent increasing the number PET scanners. Additionally, with sparse rings configuration, a PET scanner with standard axial FOV can include fewer (e.g., half) detector rings, yielding a significant reduction in manufacturing costs.

When an example PET scanner of the present disclosure is operated in a retracted axial FOV, the PET scanner can provide increased sensitivity to provide an increased signal-to-noise ratio. In some implementations, the PET scanner of the present disclosure can be configured with an axial gap sufficiently large for in-beam radiotherapy treatment delivery and validation.

Referring to FIG. 1, in various embodiments, a system 100 may include a computing device 110 (or multiple computing devices, co-located or remote to each other) capable of communicating with an imaging system 150, which may include, for example, a PET imaging system and/or other imaging systems, devices, cameras, sensors and detectors (e.g., a computed tomography (CT) imaging system if the imaging system 150 is a PET-CT system). In various embodiments, computing device 110, or portions thereof, may be integrated with imaging system 150. In other embodiments, computing device 110 may be separate from, and in wired and/or wireless communication with, the imaging system 150. A transceiver 112 may be used by the computing device 110 to exchange readings, control commands, and/or other data with imaging system 150 or components thereof, or with other systems and devices.

The imaging system 150 may include a scanner 154, which includes sensors, cameras, etc., for capturing physiological signals corresponding to subjects being scanned. In a PET imaging system, for example, the scanner 154 may include detector rings, such as a set of parallel detector rings. The scanner 154 may include one or more detector elements 156, such as detector elements that form the detector rings of scanner 154. In a PET imaging system, the detector elements may be, for example, gamma ray or other radiation detectors elements. In some embodiments, the scanner 154 comprises a PET camera system that includes multiple rings of detector elements, which may be scintillation crystals (e.g., bismuth germanium oxide (BGO), gadolinium oxyorthosilicate (GSO), or lutetium oxyorthosilicate (LSO)) coupled with, for example, photomultiplier tubes, silicon photomultipliers (SiPM), or avalanche photodiodes (APD).

In various embodiments, the scanner may include a scanner drive mechanism 158 allowing for changes in gaps between detector rings. In some embodiments, the gaps between detector rings may be static or otherwise unchanging, with detector rings separated by, for example, fixed spacers. The detector rings may be part of or secured to detector plates, and the separation between detector rings may be adjusted by separating the plates (e.g., statically using fixed spacers between plates, or dynamically using a drive mechanism that allows for adjustment of the separations between plates). The imaging system 150 also includes a subject table 162, which may comprise a bed on which a subject is positioned for scanning. In various embodiments, the subject table is movable via a bed drive mechanism 164. The imaging system 150 may also include a gantry 152, which may include a housing for the scanner 154 and/or other components of imaging system 150. The gantry may include a gantry drive mechanism 160 that rotates or otherwise moves the detector elements of scanner 154. For example, a rotator mechanism may rotate detector rings such that detector elements change position relative to the subject (or parts thereof). This enables, for example, for repositioning of the detector elements to, for example, detect radiation that would have been missed because its path would coincide with a gap between detector rings (and would not coincide with any of the detector rings).

The computing device 110 may include a controller 114 that is configured to exchange control signals with imaging system 150 (or components thereof), allowing the computing device 110 to be used to control the capture of images and/or signals via sensors of the imaging system 150, retrieve imaging data or signals, direct analysis of the data and signals, and output analysis results. The controller 114 may include one or more processors and one or more volatile and non-volatile memories for storing computing code and data that are captured, acquired, recorded, and/or generated. The controller 114 may include hardware and/or software for controlling different components of the imaging system 150. For example, controller 114 may include a scanner controller 116 for controlling the scanner 154 (e.g., via control signals to scanner drive mechanism 158 to adjust gaps between detector rings), a subject table controller 118 for controlling the subject table 162 (e.g., via control signals to bed drive mechanism 164 to bring a subject on the subject table 162 into gantry 152 for scanning), and/or a gantry controller for controlling the gantry 152 (e.g., via control signals to gantry drive mechanism 160 to rotate or otherwise reposition scanner 154 or detector elements 156 thereof).

One or more user interfaces 118 allow the computing device 110 to receive user inputs (e.g., via a keyboard, touchscreen, microphone, camera, etc.) and provide outputs (e.g., via a display screen, audio speakers, etc.). The computing device 110 may additionally include one or more databases 124 for storing, for example, data or signals acquired via one or more imagers or other sensors. In some implementations, database 124 (or portions thereof) may alternatively or additionally be part of another computing device (that is co-located or remote and in communication with computing device 110) and/or of imaging system 150.

Computing device 110 may include a data acquisition module 130 that acquires images or signals (collectively, imaging data) via imaging system 150. In certain embodiments, data acquisition module 130 may access imaging data, acquired through past scans, from database 124 or another system or device. The data acquisition module 130 may, in some embodiments, request and receive particular imaging data from the imaging system 150, or may receive all imaging data from imaging system 150 and identify particular subsets thereof that are to be used for various analyses. In some embodiments, data acquisition module 130 may control or direct imagers and/or sensors of imaging system 150 to capture various images or signals, or may direct components of imaging system 150 to provide certain raw or processed data.

A data processing unit 134 may receive imaging data from data acquisition module 130 and analyze the imaging data. The data received from data acquisition module 130 may be raw or processed. Data processing unit 134 may analyze imaging data to, for example identify physiological characteristics or metrics in a region of interest (ROI) that is scanned using imaging system 150. The data processing unit 134 may include an interpolator 136, which may be configured to, for example, apply an axial projection interpolation model to infer missing measurements due to the gaps between detector rings. In various embodiments, the interpolator 136 may help address any noise enhancement expected from the reconstruction of axially sparse PET data. Data processing unit 134 may include a normalizer 138, which may be configured to implement a component-based normalization model to sparse and interpolated PET data to account for the sensitivity of the scanner at gaps before and/or after interpolation. Normalized sparse PET data from normalizer 138 may be subsequently used by, for example, image reconstructor 140, such as in three-dimensional (3D) PET image reconstruction, to produce image quality comparable to that of compact ring PET scanner configurations.

Figure 2:
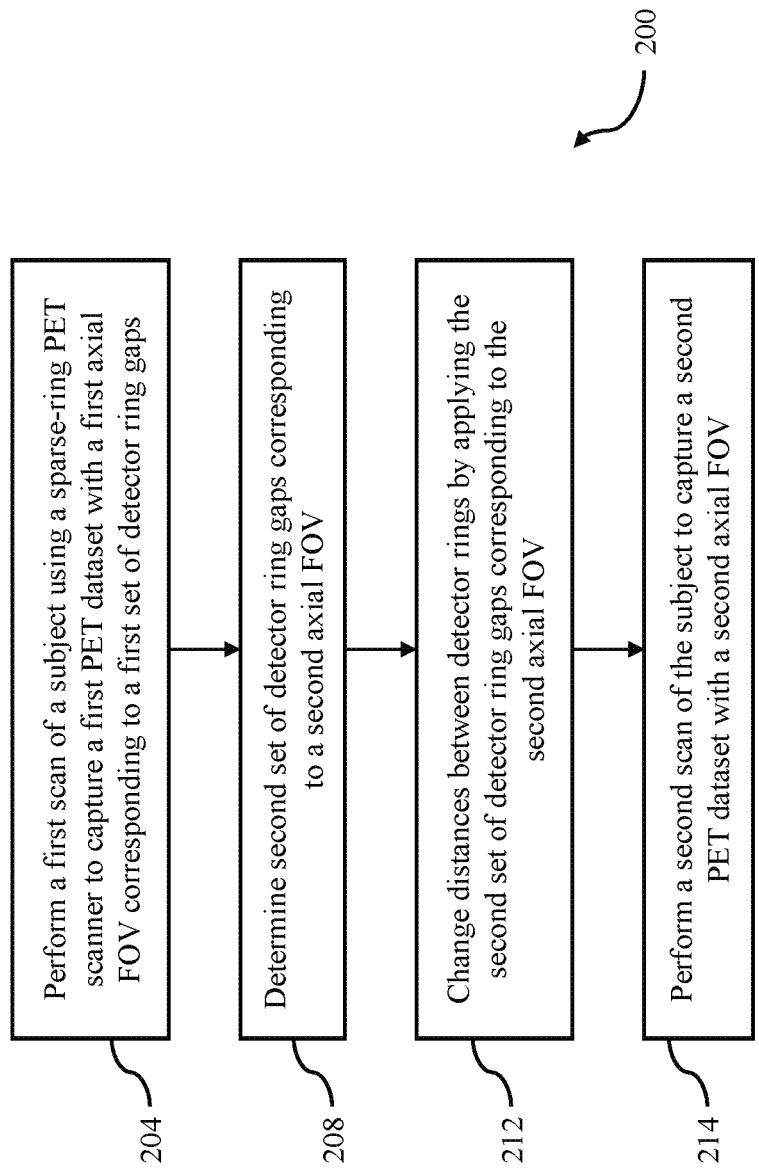
FIG. 2 depicts an example flow chart illustrating example operations involved in potential PET scans using a PET scanner having a scanner with a sparse detector ring configuration, according to potential embodiments.

Referring to FIG. 2, an example process 200 for performing a dynamic scan using a PET scanner is provided, according to various potential embodiments. At 204, a first scan is performed using a sparse-ring PET scanner to capture a first PET dataset. In various embodiments, controller 114 of computing device 110 may initiate and perform the first scan using imaging system 150, and in particular, scanner 154. Controller 114 may, before, during, and/or after the first scan: make adjustments to gaps between detector rings (e.g., via scanner controller 116 sending control signals to scanner drive mechanism 158 of scanner 154) to, for example, select an axial FOV for the scan; move the subject table 162 (e.g., via subject table controller 118 sending control signals to bed drive mechanism 164 of subject table 162) to, for example, move the subject into gantry 152; and/or rotate the detector rings of scanner 154 (e.g., via gantry controller 120 sending control signals to gantry drive mechanism 160 of gantry 152) to, for example, capture signals that would have been missed due the gaps between the detector rings of scanner 154.

The first PET dataset may be received by computing device 110 and captured by data acquisition module 130. The first PET dataset may correspond to a first axial FOV (defined by, e.g., an axial width of a set of parallel detector rings) achieved through a certain set of gaps between detector rings of scanner 154. Based on the first scan, the computing device 110 may determine that a second axial FOV may be more suitable under the circumstances. A different axial FOV may be more suitable if, for example, a region of interest (ROI) is excluded from the first scan. At 208, the computing device 110 may determine (e.g., via data processing unit 134) a second set of detector ring gaps corresponding to the second axial FOV.

At 212, the controller 114 (e.g., via scanner controller 116 sending control signals to scanner drive mechanism 158 of scanner 154) may change distances between detector rings by applying the second set of detector ring gaps to the scanner 154. At 214, the computing device 110 may perform a second scan of the subject to capture a second PET dataset with a second axial FOV. Controller 114 of computing device 110 may initiate and perform the second scan using imaging system 150, and in particular, scanner 154. As with the first scan, controller 114 may, before, during, and/or after the first scan: make adjustments to gaps between detector rings to, for example, select an axial FOV for the scan; move the subject table 162 to, for example, move the subject into gantry 152; and/or rotate the detector rings of scanner 154 to, for example, capture signals that would have been missed due the gaps between the detector rings of scanner 154. In some embodiments, the second PET dataset may be analyzed to determine whether other axial FOVs are suitable and/or whether additional scans are warranted.

In various embodiments, PET cameras encompass a set of compact crystal detector rings, and in a sparse ring configuration, may comprise half the original number of rings (or otherwise fewer rings) uniformly spaced across the same axial FOV. To demonstrate the effect of such a configuration on image quality and quantitation in PET imaging, a Siemens PET/MR (mMR) system matrix was adopted in a proposed configuration. mMR consists of 64 detector rings made of 4×4×20 mm$^3$ LSO crystals, and extending over 25.6 cm axial FOV. To emulate a sparse rings configuration, counts in sinograms associated with at least one even ring number were zeroed (Sparse-Sinograms). To account for the loss in spatial information, the zeroed sinograms were estimated by linear interpolation in sinogram space (Inter-Sinogram). The PET images for the compact, the sparse, and the interpolated sparse sinogram data were reconstructed using the OSEM algorithm (21 subsets, 5 iterations) provided by the Software for Tomographic Image Reconstruction using the original mMR system matrix to maintain the same number of slices in all images. The approach was validated for one brain FDG PET/MR dataset in terms of image quality, target-to-background ratio (TBR), and contrast-to-noise ratio (CNR) scores for different number of OSEM iterations. Sparse rings configuration yielded comparable image quality to that of the clinical dataset. TBR and CNR showed increased error with the number of OSEM iterations (8.3% and 23.6% respectively at 5 iterations), decreasing to 1.7% and 5.4% respectively in the Inter-Sinogram images. PET imaging with half the number of original detector rings uniformly spaced over the same axial FOV, yielded comparable image quality, yet reduced TBR and CNR, which may be recovered via linear inter-sinogram interpolation. As will now be discussed in more detail, uniformly spacing a given set of PET detector rings to double their axial FOV does not result in significant losses in image quality and quantitation in various implementations.

PET systems typically employ a concatenated set of parallel detector rings sharing a common axis, a geometric configuration that allows for high spatial sampling rates of the axial FOV to achieve high sensitivity within a small axial FOV and superior axial spatial resolution. However, the concatenation of detectors along the axial dimension of a tomographic PET scanner without interleaving any gaps between the rings results also in the smallest possible axial FOV for a given number of rings and detectors axial pitch. Assuming a fixed number of detectors per ring, the cost of a clinical PET scanner would thus be directly proportional to the number of detector rings, as the detector crystals are the most expensive part of a clinical PET scanner. Thus, compact ring configurations are expected to yield the highest manufacturing cost per axial FOV length. As a result, clinical PET systems have been traditionally supporting only short axial FOVs (<26 cm) to retain the total cost at reasonable levels. However, short axial FOVs can drastically confine the modern capabilities of static PET imaging.

First, in single-bed 3-dimensional (3D) PET scans the 3D sensitivity is increasing with the square of the number of detector rings assuming acceptance of coincidences from all possible ring combinations. Therefore, the extension of the axial FOV to very large lengths via the proportional increase of the number of detector rings can yield a dramatic increase in volume sensitivity for a relatively less dramatic, yet considerable, increase in detector elements and, thus, in manufacturing cost. Moreover, 3D sensitivity is significantly reduced moving from the center to the edges of the axial FOV regardless of the axial FOV length. However, the sensitivity drop rate becomes steeper for shorter axial FOVs. Thus, single-bed PET scans with long axial FOVs are expected to yield images with better noise uniformity within a given central portion of the axial FOV, relative to short axial FOVs. This can be an important benefit for lesion detectability and quantification if the lesion location is unknown or it extends towards the edges of the axial FOV. Moreover, in single-bed dynamic 3D PET scans, which are often conducted over the heart, brain or pelvic regions, the noise levels are expected to increase, compared to static scans, due to the relatively shorter time frames of PET data employed. Thus, longer axial FOVs may be even more important to mitigate the amplified noise non-uniformities at a central axial FOV region.

Furthermore, short axial FOVs prevent the simultaneous imaging of multiple organs of the human body. This may restrict the investigation of systemic molecular effects between highly related but distant organs, such as the brain-heart and brain-gut axis, using sub-optimal sequential acquisitions at different bed positions. Moreover, short axial FOVs are more likely to exclude neighboring blood pool regions, such as heart ventricles, aortic segments or carotid arteries which would be necessary for full kinetic modeling and which are not always included in the short axial FOV, such as in the brain and pelvis.

In addition, multi-bed or whole-body 3D PET studies can be compromised by short axial FOVs. Whole-body FOVs are particularly important for many oncologic PET studies evaluating primary and metastatic tumor lesions across the whole body. The current generation clinical PET systems with short axial FOVs require sequential acquisitions either during a continuous bed motion or at different overlapped stationary bed positions to cover the total axial FOV of a whole-body PET exam. In either case, different sections of the axial FOV are scanned at different post injection times, which may introduce significant bias between the measurements of different bed position, if the radiotracer's dynamic distribution is changing fast at the time of imaging with respect to the time interval between the scans of the different beds.

Moreover, small axial FOVs pose a major limitation for the translation of dynamic and parametric PET imaging to the clinical routine. In particular, the detectability and quantitation of primary and metastatic lesions molecular activity at unknown locations across the human body is critical and could benefit from the combined analysis of both static and dynamic whole-body PET data. However, the confined axial FOV of modern PET systems prevents the continuous spatiotemporal sampling of a radiotracer distribution across multiple bed positions, therefore hindering the application of dynamic PET scans across more than one bed positions. As a result, full compartmental kinetic modeling is not feasible across multiple bed FOVs where, instead, the more robust whole-body Patlak graphical analysis methods have demonstrated potential. However, full kinetic modeling is necessary for a wide scope of studies specifically targeting the individual micro-parameters of compartmental kinetic models for the evaluation of the complex kinetic properties of radiotracers in oncologic and cardiovascular lesions.

PET scanners with total-body axial FOVs that rely on highly compact detector ring configurations would require a very high number of detector elements. As a result, the manufacturing cost of total-body PET scanners is currently very high preventing the translation of their important benefits to routine clinical imaging.

In the meantime, modern clinical PET systems have been gradually equipped with advanced and highly efficient electronics as well as detectors with fine time resolution to support highly sensitive fully 3D acquisitions with time-of-flight (TOF) measurement capabilities and reconstruction methods with point-spread function (PSF) modeling features. As a result, modern PET scanners can nowadays achieve significant enhancements in PET signal-to-noise ratio, image quality and lesion detectability and quantification for a given injected dosage or scan time. The attained gains in PET SNR have hitherto been exploited to design PET scanners with an improved trade-off between scan time and injected dosage while the axial FOVs have only marginally been extended. Nevertheless, the above SNR enhancements could also suggest that highly compact ring configurations may no longer be necessary to attain the image quality and lesions' contrast and quantification performance of current generation clinical PET systems.

A primary motivation for promoting an axial sparsity scheme when designing a PET system may be to either (i) double the axial FOV for the same number of detectors and therefore similar cost, or (ii) significantly reduce the scanners cost by including half the detectors rings in a sparse configuration across the same axial FOV. In various embodiments, the use of exclusively axial, as opposed to transaxial, gaps facilitates the straightforward transformation of existing compact ring configurations to sparse rings configurations and enables dynamically-adjustable axial FOVs.

Sensitivity losses at gaps between detector rings may be recovered by scanning for longer times. Moreover, simultaneous PET/MR studies can afford significantly longer PET acquisition times, relative to PET/CT studies of the same FOV size, as they are typically conduced in parallel to the often-lengthier MR sequences.

A sparse PET detectors geometry, where axial gaps of equal size are introduced between every detector ring of an existing clinical PET scanner, was assessed in-vivo, and the performance of the sparse rings configuration compared against that of the original PET scanner as well as that of a hypothetical PET system including only the half most-central original detector rings in a compact configuration.

A first comparison between the sparse and original PET detector rings configuration allows for assessment of whether any regional sensitivity losses in the gaps will significantly affect overall image quality but can reduce to some limited extent the lesions contrast and background variability (noise), compared to the original PET system. This comparison sheds light on whether sinogram interpolation can drastically reduce the elevation of noise and the losses in contrast-to-noise ratio (CNR) of the sparse versus the original PET system. A second comparison is relevant to whether image quality as well as lesions contrast and quantification of the sparse system are similar to those attained with the compact system adopting the half most-central rings configuration. In addition, the second comparison provides insights regarding the potential for the sparse system to match the lesions CNR of the compact system with the half most-central rings after sinogram interpolation.

Further, the second comparison indicates if the noise uniformity across the axial FOV of the PET images produced with the half most-central rings configuration is worse than that of the sparse rings configuration over their overlapping axial FOV.

Figure 3B:
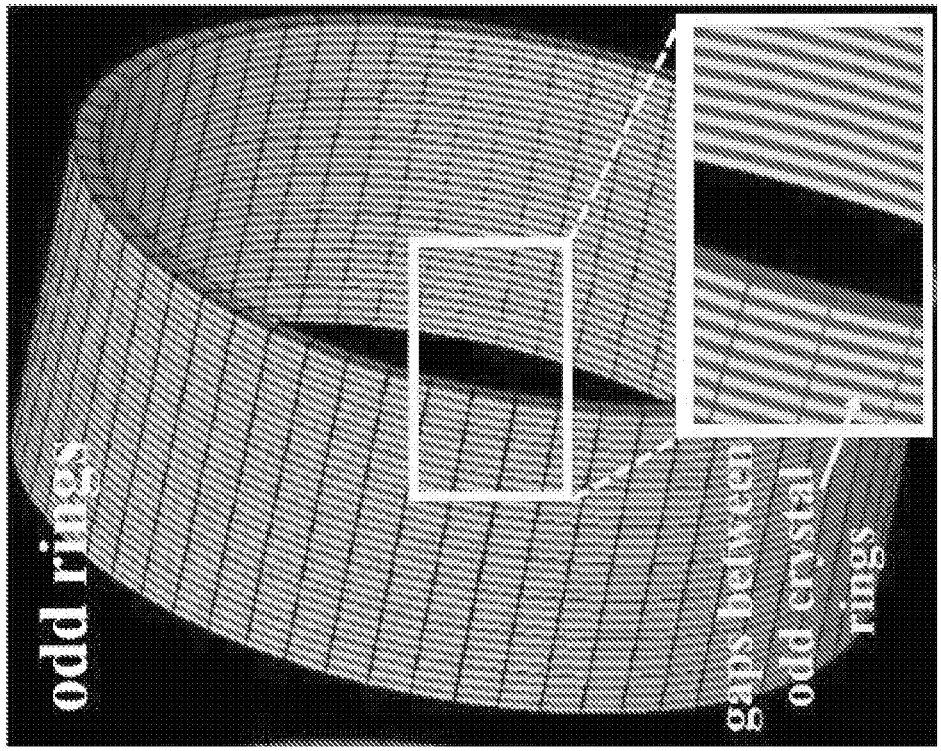
FIG. 3B depicts an "odd-rings-only" sparse PET detectors configuration, according to potential embodiments, as visualized with the GATE Monte Carlo simulation package.
Figure 3A:
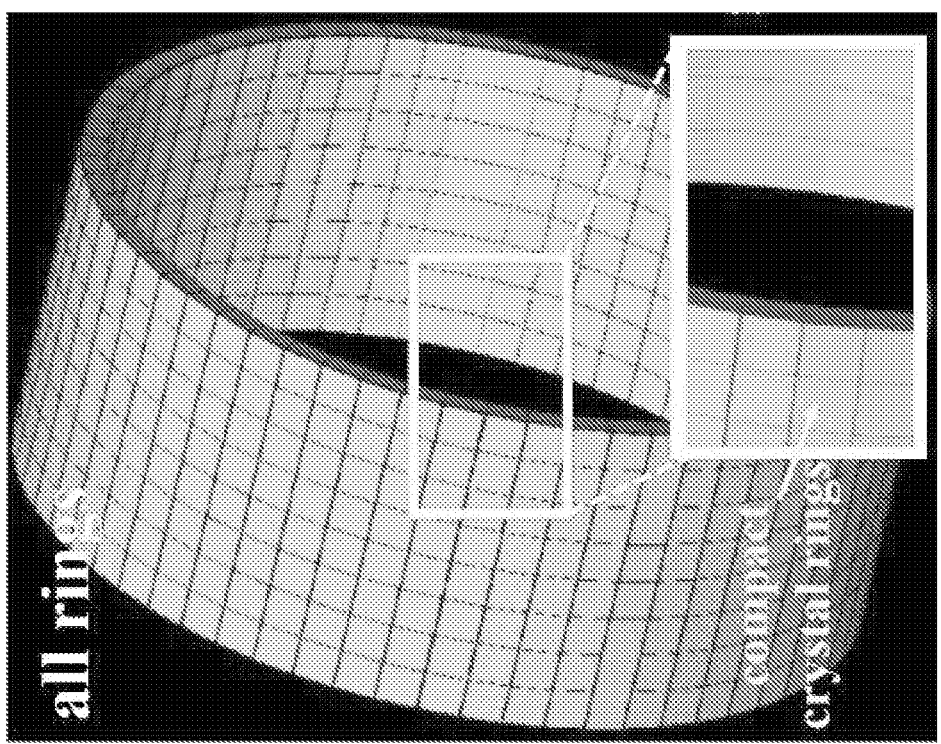
FIG. 3A depicts an actual "all-ring" compact ring configuration.

Referring to FIGS. 3A and 3B, an example embodiment involves a sparse PET detector ring configuration referred to as an "odd-rings-only" sparse-mMR system (see FIG. 3B). In order to evaluate image quality and sensitivity, the example embodiment retrospectively accessed phantom and clinical brain PET data acquired by a human PET/MR scanner and set to zero all the counts of the direct and oblique sinogram planes containing lines-of-response (LORs) associated with at least one even detector ring. The new sparse configuration resulted in the same axial FOV but with only half of the original detector rings. Subsequently, the example embodiment employed an inter-sinogram plane interpolation method to infer the projection data at the missing planes. Finally, the example embodiment used the original system matrix of the "all-rings" compact configuration (see FIG. 3A) to reconstruct the three types of data with the Software for Tomographic Image Reconstruction (STIR). For that purpose, the example embodiment accounted for the gaps in the axially uncompressed (span-1) detector space when estimating the appropriate component-based normalization, randoms and scatter correction sinograms. Thus, we example embodiment ensured the consistency between the prompt coincidence sinograms and the correction factor sinograms to avoid propagation of any artifacts during image reconstruction.

The configuration of the example embodiment can be readily emulated from existing commercial PET systems by applying an axial sparsity scheme on the fully uncompressed Michelogram structure of list-mode or histogrammed PET data acquired by any existing PET system. The new sparse rings configuration was denoted in this embodiment as "odd-rings-only" to differentiate it from the default "all-rings" compact configuration and other sparsity schemes. The compact ring configuration involves no gaps between the individual detector rings except perhaps from small axial gaps between the blocks and is the typical configurations adopted by the standard-of-care clinical PET systems nowadays.

As a gold-standard reference clinical PET scanner model (i.e., reference compact PET detector ring configuration ("all-rings")), the example embodiment used the configuration of the Siemens Biograph™ mMR PET/MR scanner currently installed in Weill Cornell Medical College, which has one of the largest axial FOVs (25.6 cm) currently available in commercial human PET systems. In various other embodiments, TOF information improves the performance of the configuration of this example embodiment by enhancing the robustness of sparsity to noise in the acquired PET data and mitigating any potential data inconsistencies as previously demonstrated for compact ring PET systems.

Although TOF technology is currently adopted by most state-of-the-art clinical PET systems, there are still highly utilized non-TOF PET systems with very unique and important capabilities that are widely used around the globe for front-end clinical and research protocols. One such example is the integrated non-TOF PET/MR Biograph™ mMR system employed in this study, which exploits the superior soft-tissue resolution, zero radiation exposure, multi-parametric imaging features and motion-tracking capabilities of MR with the wide variety of molecular imaging biomarkers and quantification of PET to enhance the diagnostic and theranostic capabilities of each of the two imaging modalities alone. The example embodiment demonstrates the sparse ring configuration and validates its performance even with clinical non-TOF PET data produced by such a highly promising PET system.

In addition, the mMR system inherently and readily supports access to axially uncompressed (span-1) list and sinogram PET data, which was important for the accurate modeling of the sparse rings configuration in a compact clinical scanner. In particular, all sinogram bins associated with detector pairs that connected at least one of the even detector rings of the original mMR configuration were assigned zero counts in the example embodiment.

With respect to the example embodiment, a Monte Carlo simulation of mMR and sparse-mMR system (physical gaps versus emptying of even rings) will now be discussed. Beside the modeling of the sparse rings configuration from a real mMR scanner, the example embodiment also involved a series of Monte Carlo realistic simulations using the Geant4 Applications for Tomography Emission (GATE) software package to visualize and compare the default mMR ("all-rings") and sparse mMR ("odd-rings-only") ring configurations (see FIG. 3B). GATE is based on the well-validated Geant4 toolkit and has been selected for the accurate simulation of the effects of the small axial gaps on the performance of a clinical PET scanner. Based on a validated Biograph mMR GATE scanner model, the example embodiment simulated a 9 min PET acquisition of a NEMA IEC phantom with a 4:1 spheres-to-background ratio.

Initially, the example embodiment defined actual physical gaps of air between the odd detector rings of the mMR GATE model to produce the realistic effects of the sparse rings configuration on the mMR detector geometry. Subsequently, the example embodiment replaced the mMR detectors with the mMR gamma photon detector crystals and emptied their coincidence counts to reproduce the sparse ring configuration model derived by the real Siemens Biograph mMR scanner. Finally, the example embodiment compared the performance of the two simulated sparse configurations in terms of NEMA IEC phantom image quality, spheres contrast and background variability. This comparison was designed to shed light to indicate that substituting the air material in the gaps with the mMR gamma photon detector crystal material would have a negligible effect on the performance of the sparse-mMR and, therefore, the sparse rings configuration model derived from a real mMR scanner after ignoring all counts from even rings would be sufficiently realistic.

A half most-central compact PET detector rings configuration ("half most-central") with respect to a half-mMR system will now be discussed. In addition to the original and sparse mMR ring configurations above, the real mMR data was used to model a hypothetical mMR-based compact ring scanner comprised of the half most-central mMR detector rings ("half most-central" ring configuration). This configuration allowed the performance comparison between a compact and a sparse mMR ring configuration that cover the same axial FOV but with the latter employing only half the detector rings of the former. Thus, it became possible to directly demonstrate on a real clinical PET scanner the effect of expanding its axial FOV by spacing out a given set of detector rings. In addition, this comparison allowed for modeling of the performance that a modern clinical PET scanner would attain after reducing its detectors to half but maintain the same axial FOV.

Inter-plane axial interpolation of the sparse 3D sinogram (interp-sparse-mMR system) will now be discussed. The "odd-rings-only" sparse mMR configuration of the example embodiment resulted in emptying all PET coincidence counts from the sinogram planes of segments corresponding to odd ring differences. Moreover, in the remaining segments, all counts in sinogram planes associated with at least one even ring were also emptied. Thus, it was expected that the signal-to-noise ratio is considerably lower, compared to the compact "all-rings" configuration.

With reference to FIGS. 4A-4D, a sinogram linear interpolation method was applied on the sparse sinogram 3D space to infer the missing counts in the empty sinogram planes (gap-planes) corresponding to the axial gaps of the sparse rings configuration. The example interpolation takes place in two sequential steps as illustrated in the 3D full sinogram format of FIGS. 4A-4D also known as Michelogram. In step 1, each pair of neighboring non-empty planes along the same Michelogram diagonal direction (FIG. 4C) are interpolated to each other to infer the missing plane located between them in the same diagonal. Subsequently, in step 2, the neighboring pairs of planes with original measurements and inferred data from step 1 are again linearly interpolated along the rows and columns of the 3D Michelogram to infer the data in the remaining gap-planes between them. As the interpolation occurred only across different direct and oblique sinogram planes and not across bins of the same plane, this method was denoted as "inter-plane" axial sinogram interpolation.

Since the proposed interpolation was applied over relatively small axial gaps equal to the axial size of each detector element (4 mm in the case of the Biograph mMR), it was expected to introduce a limited extent of axial blurring but significantly reduce the noise levels in the 3D reconstructed images especially for low-count PET frames. The example embodiment thus investigated its performance in reducing the background variability (noise) and recovering the CNR losses due to the axial gaps of the sparse rings configuration.

To retain the data consistency between the interpolated emission data and correction factors the example embodiment applied the disclosed interpolation method in the prompts, randoms and scatter data. Then the example embodiment recalculated the component-based normalization correction factors accounting for the interpolated data and repeated the 3D-OSEM PET reconstructions.

Regarding image quality and lesion detectability evaluation metrics, in the reconstructed PET images from all Biograph™ mMR ring configurations presented above, the example embodiment identified target lesions and their background in both the phantom and the clinical PET/MR studies. Subsequently, the reconstructed PET image quality was evaluated visually, in terms of artifacts and visual detectability of the targeted lesions. Finally, the example embodiment measured the target-to-background ratio (TBR) and contrast-to-noise ratio (CNR) scores in the target regions as a function of the 3D-OSEM reconstruction iterations. The TBR and CNR quantitative scores were defined as follows:

$$TBR = \frac{SUV_{mean}^{target} - SUV_{mean}^{background}}{SUV_{mean}^{background}} \quad (1)$$

$$CNR = \frac{SUV_{mean}^{target} - SUV_{mean}^{background}}{SUV_{std_{dev}}^{background}} \quad (2)$$

where $SUV_{mean}$ and $SUV_{std\_dev}$ denote the mean and standard deviation of the standardized uptake values (SUV) across all the pixels of the respective region of interest.

Figure 5C:
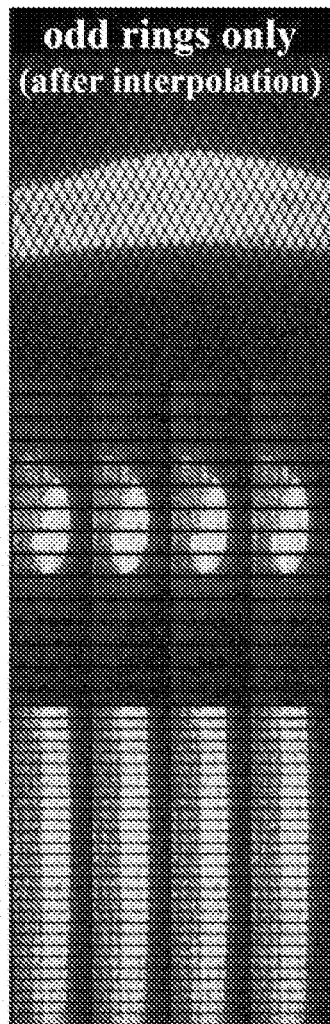
FIGS. 5A-5C depict sinograms ordered in segment 0, +/−1, +/−2, . . . order for "all-rings" (FIG. 5A), "odd-rings-only" (FIG. 5B), and "odd-rings-only after interpolation" (FIG. 5C) set-ups.
Figure 5B:
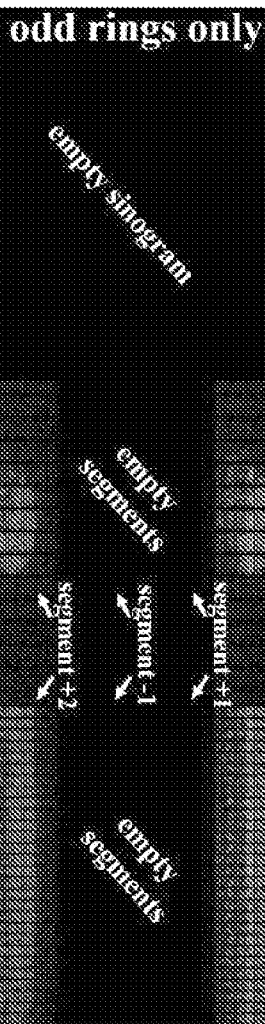
Figure 5A:
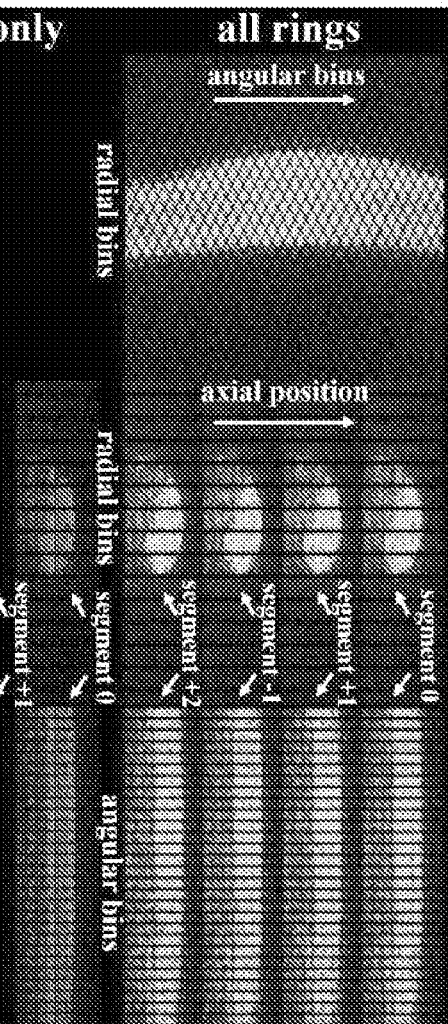

With respect to FIGS. 5A-5C, examples of the counts distribution from different segments of the 3D PET sinograms for the original mMR (FIG. 5A, all-rings) and the sparse mMR (FIG. 5B, odd-rings-only) geometries are presented. Furthermore, the comparison of the above distribution with the interpolated sinogram counts distribution illustrated the "gap-filling" effect of inter-plane axial sinogram interpolation on the sparse mMR data (see FIG. 5C). Note that, initially, all sinogram planes of all segments corresponding to odd ring differences were completely empty due to the introduced gaps in place of the even mMR rings. Thanks to the 2-step axial interpolation scheme on the sparse 3D sinogram, it became possible to infer all the missing counts without significant loss in resolution and contrast. No apparent visual differences were found after carefully inspecting the original 3D mMR sinogram with that inferred from axial interpolation of the sparse mMR data. A similar observation was made later in the reconstructed images.

Figure 6:
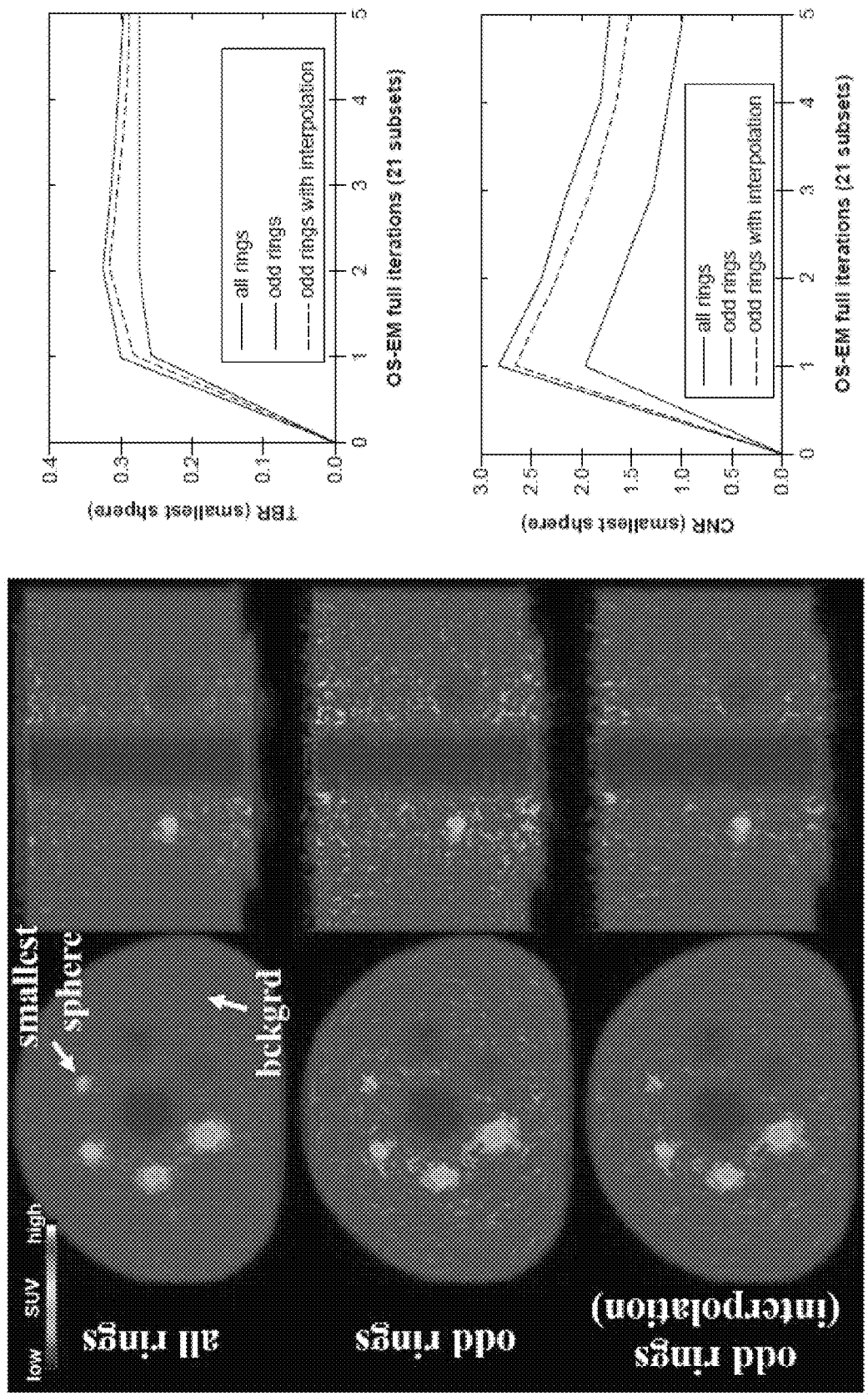
FIG. 6 depicts: in the two left columns, 18F-FDG NEMA IEC phantom images (5-min mMR scan, 4:1 spheres-to-background contrast, OSEM, 2 iterations, 21 subsets); all-ring (first row), odd-rings (2nd row), and odd-rings with interpolation (3rd row); TBR (right column, at top) and CNR (right column, at bottom) plots of the smallest sphere across the first 5 OS-EM iteration, where TBR=(SUVmean$_{sphere}$−SUVmean$_{bckgrd}$)/SUVbckgrd and CNR=SUVmean$_{sphere}$−SUVmean$_{bckgr}$, according to potential embodiments.

FIG. 6 presents experimental NEMA IEC image quality (IQ) phantom data acquired with the Siemens Biograph mMR system according to the NEMA NU 2-2007 standards with a 4:1 spheres-to-background contrast for 5-min. This experiment allowed the performance evaluation of the sparse "odd-rings-only" configuration, before and after axial linear interpolation of the acquired sparse sinogram, against the original "all-rings" mMR configuration.

These acquisitions were repeated with the GATE Monte Carlo simulation package using a validated model of the original mMR scanner and later introducing actual physical air gaps to model the sparse-mMR configuration. No significant discrepancies between the real and the GATE qualitative and quantitative results were found for the level of counts acquired in the two experiments.

The visual inspection of the PET images revealed no important differences or artifacts due to the introduced axial gaps. A slight noise elevation in the background regions can be observed for the sparse data, which is nearly eliminated after applying axial interpolation on the sparse sinogram. All spheres can be clearly resolved in both configurations regardless of interpolation. In addition, the sparse configuration attained for the smallest sphere (10 mm diameter) on average 6% less TBR and 19% less CNR than the original mMR configuration. The worse CNR performance is attributed to the noise elevation in the background due to the reduced sensitivity by a factor of 4 expected when reducing the number of detectors by a factor of 2. Nevertheless, the smaller effect on TBR suggests that the axial gaps presence did not affect quantification and contrast recovery.

The axial interpolation of the sparse sinograms improved slightly the TBR. However, more significantly, the CNR performance of the sparse mMR reconstruction was drastically enhanced after interpolation thereby reducing its discrepancy from the original mMR CNR performance to 7%. The large CNR improvement can be attributed to the considerable noise reduction attained with interpolation. To the contrary, the relatively small TBR improvement can be explained by the axial blurring introduced from the interpolation, which counteracted any potential contrast enhancements.

Moreover, the TBR differences between the sparse and the original mMR configuration appear to reduce for larger iterations. This can be explained by the relatively slower convergence rate expected of 3D-OSEM reconstructions of highly noisy data, as it is the case with the sparse mMR data in the study. On the other hand, the respective CNR differences were insensitive to the number of 3D-OSEM iterations because the relatively higher noise levels of the sparse mMR data were increasing with iterations at a higher rate compared to the original mMR data.

Figure 7:
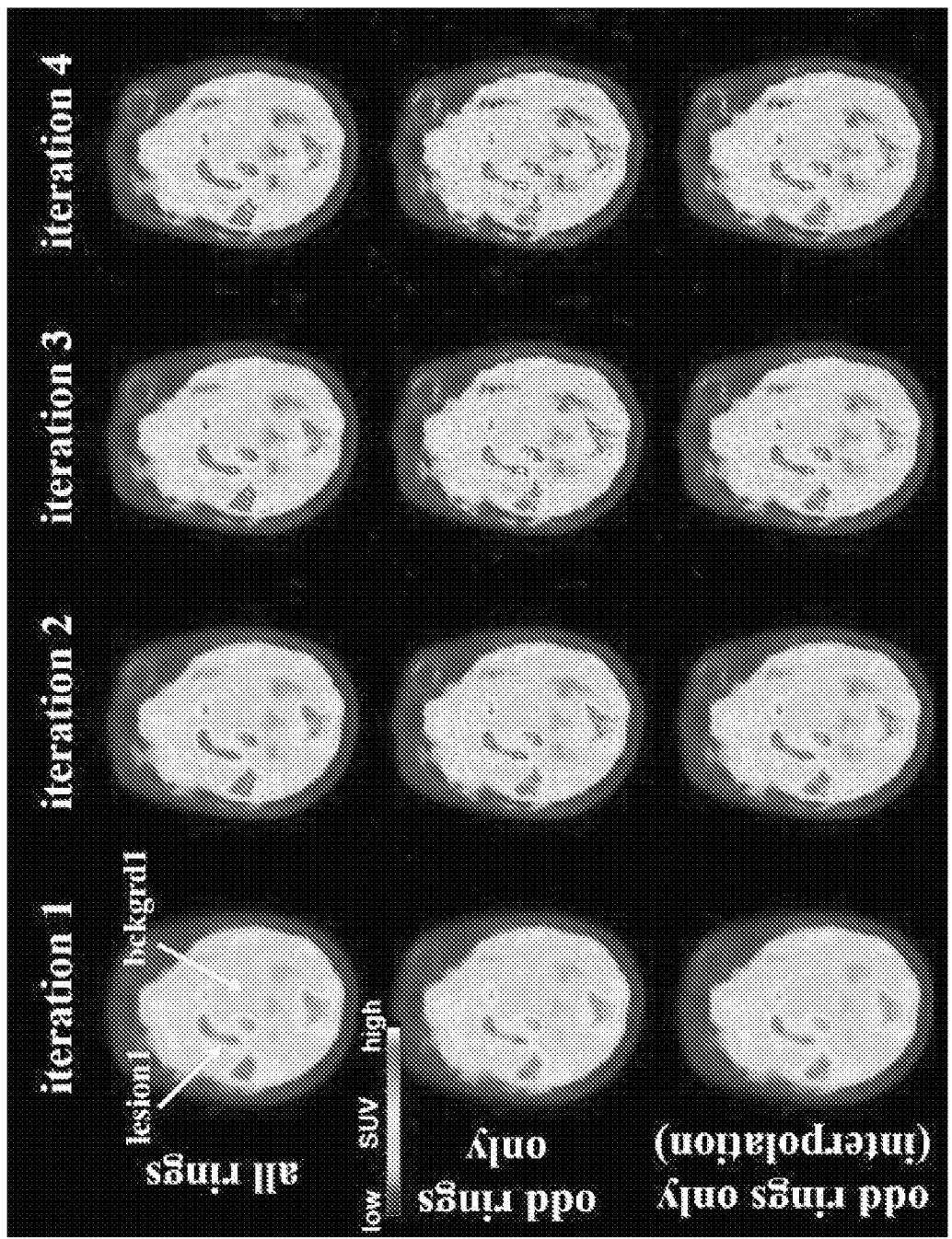
FIG. 7 depicts transaxial PET images from a human 18F-FDG PET/MR brain study across 4 full OS-EM iterations (21 subsets) acquired with a Siemens Biograph™ mMR scanner and using STIR to reconstruct from: (top-row) original "all-rings" configuration, (middle row) and sparse "odd-rings-only" without interpolation and (bottom row) with inter-plane axial sinogram interpolation, according to potential embodiments.
Figure 8:
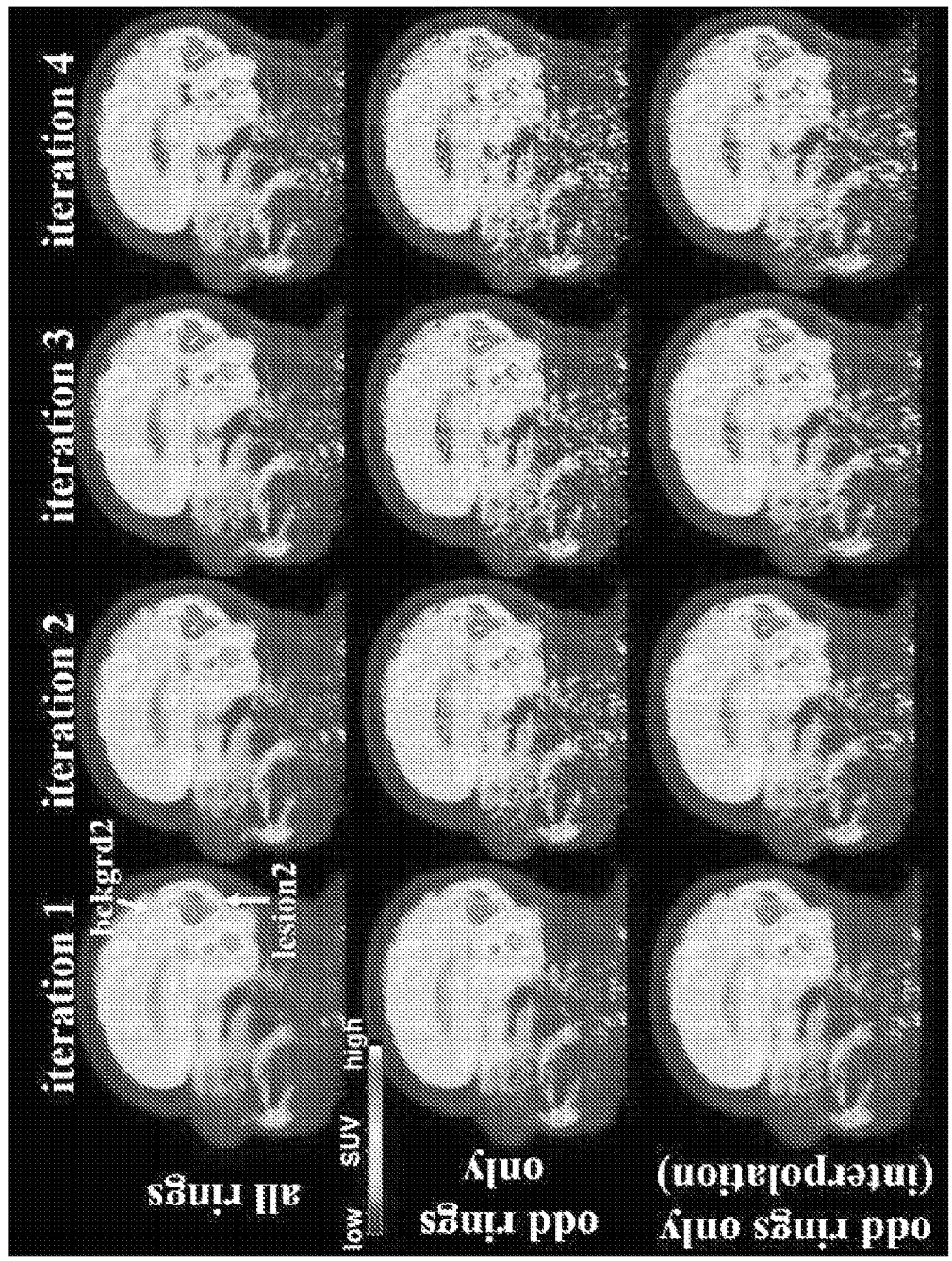
FIG. 8 depicts sagittal PET images from a human 18F-FDG PET/MR brain study across 4 full OS-EM iterations (21 subsets) acquired with a Siemens Biograph™ mMR scanner and using STIR to reconstruct FROM: (top-row) original "all-rings" configuration, (middle row) and sparse "odd-rings-only" configuration without interpolation and (bottom row) with inter-plane axial sinogram interpolation, according to potential embodiments.

FIGS. 7 and 8 provide two characteristic examples the in-vivo image quality performance of reconstructed PET data acquired with the sparse "odd-rings-only" configuration without and with inter-plane axial sinogram interpolation against the same data acquired with the original mMR "all-rings" configuration. The PET images reconstructed from the sparse and interpolated sinograms did not exhibit artifacts due to the introduced axial gaps. In addition, all phantom spheres and identified brain lesions were clearly resolved in both datasets. However, slightly elevated noise levels in the PET images reconstructed from sparse-mMR data were observed.

Figure 9:
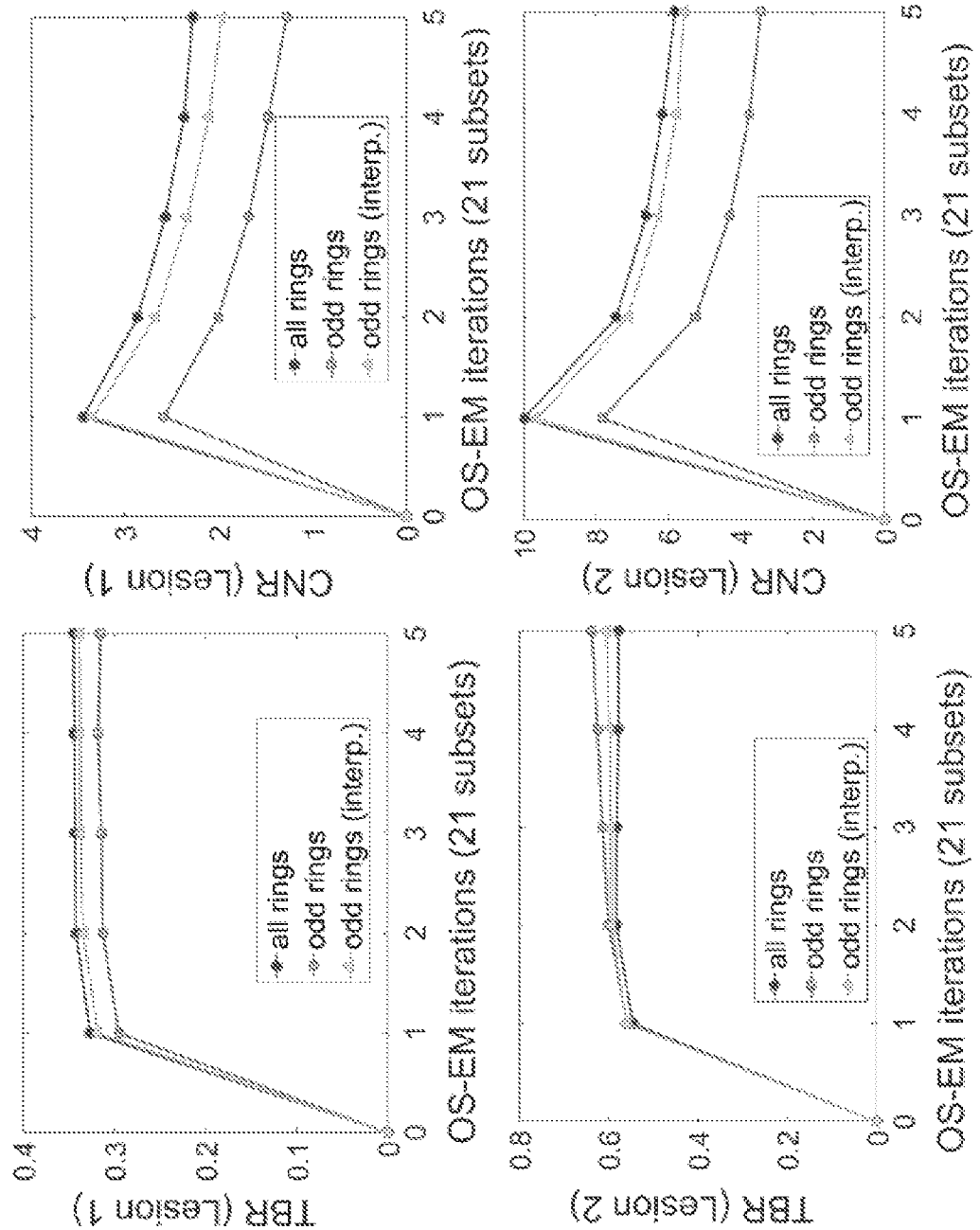
FIG. 9 depicts target lesion-to-background ratio (TBR) and contrast-to-noise ratio (CNR) scores versus OS-EM full iterations (21 subsets) for two different lesions, as denoted in FIG. 5, according to example embodiments.

The respective quantitative target-to-background (TBR) contrast and contrast-to-noise ratio (CNR) results are presented in FIG. 9. The TBR scores attained with the sparse-mMR configuration across all evaluated phantom and brain regions were at most 8.3% less than that of the mMR. After sinogram-based interpolation, the interp-sparse-mMR TBR scores became at most 1.7% lower than that of mMR. Furthermore, although sparse-mMR yielded a higher background variability and lower CNR by a maximum of 23.6%, compared to mMR, this difference was reduced to less than 5% after applying the proposed axial interpolation on the sparse sinograms.

The example embodiment validated sparse PET detector rings configurations for existing clinical PET geometries using non-TOF PET data as a worst-case scenario. Using real phantom and clinical PET data acquired with the current state-of-the-art Siemens Biograph mMR scanner, example embodiment was able to emulate the proposed sparse rings configuration (sparse-mMR) by removing all measured coincidence counts associated with at least one of the even detector rings of the original mMR system. Performance evaluation was conducted on NEMA IEC IQ phantom and human brain PET/MR scans employing the proposed sparse rings configuration before (sparse-mMR) and after sinogram interpolation (interp-sparse-mMR) as well as the original mMR configuration as a gold standard reference. Furthermore, example embodiment also emulated a compact ring configuration using only the half most-central mMR detector rings (½ central-mMR) to allow comparison of our sparse configuration performance against that of a hypothetical mMR compact ring scanner with as many detector rings as those of the sparse-mMR system.

The PET images reconstructed from sparse and interpolated sinograms did not exhibit artifacts due to the axial gaps in the detector space. In addition, all phantom spheres and identified brain lesions were clearly resolved in both datasets. However, elevated noise levels were observed in the PET images reconstructed from the sparse-mMR data. The TBR scores attained with the sparse-mMR configuration across all evaluated phantom and brain regions were at most 8.3% less than that of the mMR. After sinogram-based interpolation, the interp-sparse-mMR TBR scores became at most 1.7% less than that of mMR. Furthermore, sparse-mMR yielded a higher background variability and lower CNR by a maximum of 23.6% compared to mMR with the respective difference being reduced to less than 5% after interpolation of the sparse sinograms. Although sparse-mMR yielded higher background variability and lower CNR than ½central-mMR by a maximum of 16%, it achieved similar TBR contrast scores and better noise uniformity than 1/central-mMR across the axial FOV of the 1% central-mMR.

The sparse configuration, in various embodiments, permits the exchange of sensitivity per transverse slice with longer axial FOVs without compromising total volume sensitivity, contrast and quantification. Such a PET system can be beneficial, for example, for any of the aforementioned PET imaging applications that are limited from the current short axial FOVs but do not anticipate better scan time for a given injected dosage and vice-versa. The same approach is scalable to even longer axial FOVs, including total-body FOVs, at half the cost that would have been required for a non-sparse ring geometry. On the other hand, the same approach could be exploited towards the reduction of modern PET systems manufacturing cost without sacrificing axial FOV. In any case, the degree of compactness of the PET detector rings may be a parameter to be optimize when designing clinical PET systems.

In various embodiments, clinical PET imaging uses sparse rings configurations including only the even detector rings of a modern clinical PET scanner. Validation on real phantom and human data obtained from a sparse rings geometry of the Siemens Biograph™ mMR scanner showed that the proposed configuration can achieve similar visual image quality and lesions' TBR contrast with current generation compact rings PET systems at significantly reduced manufacturing cost or with significantly longer axial FOVs. The reduced costs may allow the wider utilization of clinical PET systems by the world population, whereas the longer axial FOVs would permit simultaneous imaging of larger areas in the human body to enable new exciting clinical PET imaging applications without additional cost.

In various embodiments, the objective of the second configuration would be to exchange volume and per transverse slice sensitivity with reduced manufacturing cost without compromising contrast, quantification and axial FOV. This approach exploits axial sparsity for a very different purpose, which is the introduction to the world market of an economy PET scanner at nearly half the cost of the standard clinical PET systems and without compromising axial FOV size. The effect on background variability (noise) and detectability due to the inevitable reduction in volume sensitivity and sensitivity per length of axial FOV could be compensated by adjusting the scan time versus injected dosage trade-off accordingly, for instance by increasing the scan time. This solution could suit the budget of smaller PET imaging facilities with limited patient throughput where the increase in scan time per patient may not be an issue. In addition, in various embodiments, the disclosed approach enables economic PET/MR systems, which are expected to be otherwise more expensive than respective PET/CT system. Besides, the often-longer periods required for the completion of MR sequences series could permit the parallel execution of longer in time PET acquisitions without affecting the total scan time for most scan protocols. Moreover, the current clinical utilization of the relatively expensive PET/MR systems across the United States primarily for MR and much less for PET/MR exams, due to current insurance reimbursement policies, could justify the preference to more cost-efficient PET/MR systems as the effect of longer PET scan times to the daily clinical patient throughput could be anyways minimal.

In various embodiments, although noise may increase with iterations and may be relatively higher in the case of the "odd-rings-only" sparse configuration, noise may be suppressed after applying interpolation. The lesions contrast in the two designated lesion regions is similar across the three methods with no significant visual differences before and after interpolation. In the case of CNR losses for the "odd-rings-only" configuration, due to the removal of the counts associated with even rings detectors, the disclosed inter-sinogram interpolation may facilitate almost complete recovery of the CNR losses, thanks to the suppression of noise at sinogram space (see FIG. 7). Moreover, less apparent visual effects are observable between the two configurations in the transaxial (FIG. 7) versus sagittal (FIG. 8) slices, which may be attributed to the occurrence of such effects primarily along the axial direction.

As suggested, there is a growing interest in extending the AFOV of PET scanners. One major limitation for the widespread clinical adoption of such systems is the multifold increase in the associated manufacturing costs. In a second example embodiment in which Monte Carlo (MC) simulations were used to validate the physical performance of an extended AFOV PET scanner prototype by means of a sparse detector rings configuration, an MC model of the Siemens Biograph™ mCT PET/CT, with a 21.8 cm AFOV and a set of compact rings of LSO crystals was developed as gold standard. The mCT configuration was then modified by interleaving the LSO crystals in the axial direction within each detector block with 4 mm physical gaps (equivalent to the LSO crystal axial dimension) thus extending the AFOV to 43.6 cm (Ex-mCT). The physical performances of the two MC models were assessed and then compared using the NEMA NU 2-2007 standards. Ex-mCT showed less than 5% difference in transaxial spatial resolution, and ~6% and 17% deterioration in axial spatial resolution at the center and ¼ of the axial FOV respectively. The system sensitivities for the mCT and Ex-mCT models were 9.23±0.2 cps/kBq and 10.43±0.19 cps/kBq respectively. PET images of the NEMA Image Quality (IQ) phantom showed no artifacts due to detector rings sparsity, and all spheres were visible in both configurations. Ex-mCT achieved percent contrast recoveries within 2.6% of those of the mCT for all spheres and up to 36% higher background variability. The noise levels were more uniform across the axial direction of the NEMA-IQ phantom for the Ex-mCT. Using the disclosed sparse detector rings configuration, the AFOV of current generation PET systems can be doubled while maintaining the original number and volume of detector crystal elements, and without jeopardizing the system's overall physical performance. Despite an increase in the noise level, the Ex-mCT exhibited an improved noise uniformity.

Positron emission tomography (PET) is a noninvasive molecular imaging technique widely used in clinical oncology, neurology and cardiology to study physiology, metabolism, and molecular pathways in the human body. PET applications, however, have been limited to single organ imaging at a given scan time due to the limited AFOV— typically 15 cm to 26 cm in length—of current generation clinical scanners. Longer scan ranges may be achieved using either a step-and-shoot approach, where PET data are acquired sequentially at multiple bed positions, or a smooth continuous bed motion approach.

Current commercial PET scanners encompass sets of compact rings of scintillating crystals to maximize the system sensitivity per unit millimeter along the AFOV, hence maximizing the signal-to-noise ratio in the corresponding transaxial PET images. A PET AFOV of 50 cm or longer may allow reducing the scan time for a given injected radiotracer dose, especially for whole-body PET protocols, or equivalently reducing the injected radiotracer activity dosage for a given scan time, a key benefit in pediatric and longitudinal studies. Moreover, it enables simultaneous and continuous imaging over larger regions of the human body to permit multi-organ full kinetic modeling (e.g. brain and heart) at a single bed position with a variety of blood pool regions included in the now-extended FOV to deduce an image-derived input function. Thus, it may extend the limits of PET research particularly in what relates to multi-organ interactions (e.g. heart-brain PET signal interactions denoting systemic relationships between neurological and cardiovascular diseases), or multi-organ imaging with short half-lives radiotracers (e.g. $^{15}$O water), which would require injecting multiple radiotracer doses otherwise (e.g. simultaneous cardiac output/cerebral blood flow studies). In a hybrid PET/MR (Magnetic Resonance Imaging) setting, an extended AFOV PET will also allow matching the MR AFOV (~50 cm). One major limitation for the wide clinical adoption of long AFOV PET scanners is the considerable additional cost associated with the increased detector elements required. Nevertheless, the redundancies in 3D counts and the improved accuracy in Time-of-Flight (TOF) measurements of modern PET systems supports an alternative and cost-effective solution to extend the AFOV. In 3D PET, oblique tomographic planes are explicitly incorporated in the image reconstruction process. This allows partial compensation for any missing counts as in the case of physical gaps in between the detector blocks in PET systems, thus allowing to treat those as virtual detectors in the reconstruction system matrix. Furthermore, improvement in timing resolution in PET technology has allowed time-of-flight (TOF) measurements, which can effectively compensate for the reduction in signal-to-noise ratio (SNR) when employing reduced number of detectors in a PET system.

Therefore, the advent of 3D and TOF PET image reconstruction shall allow the reduction in the total number of detector elements in a PET system without jeopardizing the final image quality. In various embodiments, 3D image reconstruction allows maintaining the image quality and lesion detectability in a PET system with hypothetical sparse detector rings configuration (sparsity was achieved by zeroing the counts corresponding to even transaxial planes in the sinogram space). MC studies show good image quality of an extended AFOV PET scanner with sparse detector rings, according to various implementations.

In the second example embodiment, realistic MC simulations validate a cost-effective PET scanner prototype, Ex-mCT, with an AFOV of 43.6 cm which is double that of the mCT scanner (21.8 cm). The longer AFOV is attained by uniformly spacing out the detector rings over a larger axial distance. The individual crystals are interleaved by axial gaps of equal dimension as the crystals axial dimension. The physical performance of the Ex-mCT is assessed according to the NEMA NU 2-2007 (National Electric Manufacturers Association 2007) standards (2007) and compared against that of the mCT (gold standard). TOF is not included in the study corresponding to the second example embodiment.

Regarding MC simulations for the second example embodiment, the two scanner geometries, phantoms, sources, and physical interactions of positrons and gamma photons were simulated using the GEANT4 application for tomographic emission (GATE) Monte Carlo package. GATE was developed by the OpenGATE collaboration as an extension of the open source GEANT4 Monte Carlo toolkit and the ROOT object oriented data analysis framework. MC simulations were first carried out for the mCT (gold standard), and then for the Ex-mCT models.

In the second example embodiment, the mCT MC model was simulated as a cylindrical geometry with 40.4 cm and 42.6 cm inner and outer radii respectively. The scanner model encompassed 4 block rings, each with 48 detector blocks. Each detector block was 52×52×22 mm³ and included a compact 13×13 LSO array coated with 0.5 mm thick plastic. Each individual LSO crystal was 4×4×20 mm³. The mCT model had a total of 52 detector rings organized in 4 block rings interleaved with 3 axial gaps of 3.3 mm width each. Those gaps were treated as virtual detector rings, as per the mCT system configuration, yielding a total of 55 detector rings and an AFOV of 21.8 cm. The energy deposited upon gamma interactions in the LSO was integrated over the whole detector block where the interaction occurred and the position of interaction was assigned to the crystal with the highest deposited energy. A coincidence time window of 4.1 ns and an energy window of 435-650 keV were used. A dead time of 650 ns was used in all simulations.

For the Ex-mCT, the MC model of the mCT was adopted, however with eight axial detector block rings, yielding an AFOV of 43.6 cm. Each Ex-mCT detector block included 7 (axial)×13 (transaxial) LSO crystals with same overall dimensions as the mCT detector block. The LSO crystals of each block were interleaved with 4 mm gaps along the axial direction, equal to the axial dimension of each LSO crystal. This resulted in a uniformly sparse LSO rings configuration with a total of 56 LSO detector rings (compared to 52 in the case of mCT).

Figure 10A:
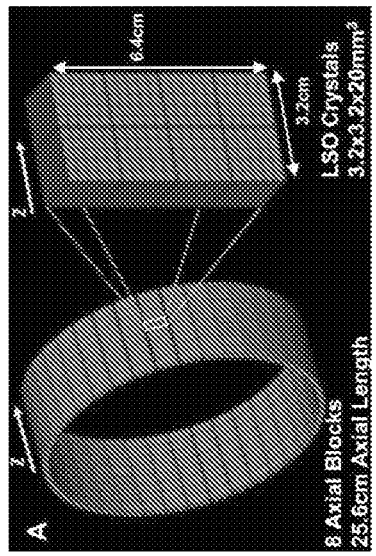
FIGS. 10A and 10B illustrate example detector configurations for mCT (FIG. 10A) and Ex-mCT (FIG. 10B), according to potential embodiments. The axial field-of-view (AFOV) of the mCT was almost doubled by spacing out the scintillators in each detector block with four millimeter (mm) physical gaps along the axial direction (small arrows in FIG. 10B depict gaps between crystals in illustrative zoomed-in snapshots).
Figure 10C:
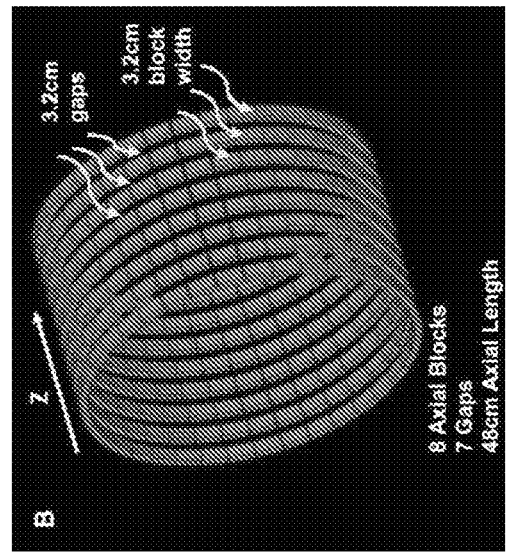
FIGS. 10C and 10D illustrate alternative example detector configurations, according to potential embodiments, where FIG. 10C provides an example compact configuration
Figure 10B:
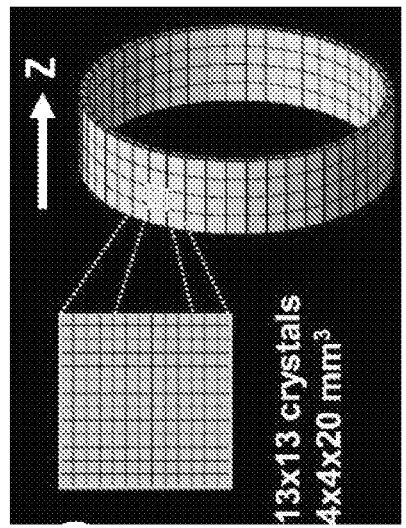
Figure 10D:
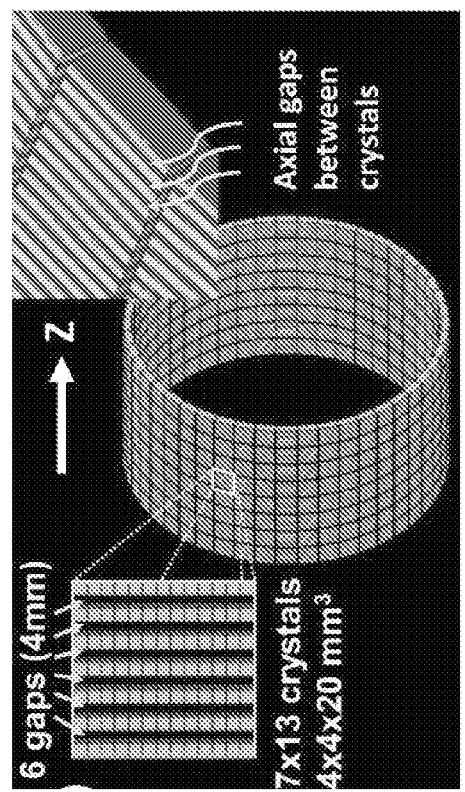

In all simulations, physics interactions were simulated using the processes listed in Table 1. FIGS. 10A and 10B depict the distribution of the axial detector rings inside the blocks in the mCT and Ex-mCT configurations.

TABLE 1

Particles and their corresponding interaction processes as simulated in GATE based on GEANT4 physics processes and implemented models

| Particle | Process | Model |
| --- | --- | --- |
| gamma | Photoelectric Effect | StandardModel |
|  | Compton Scattering | StandardModel |
|  | Rayleigh Scattering | PenelopeModel |
| electron | Ionization | StandardModele- |
|  | Bremsstrahlung | StandardModele- |
|  | Multiple Scattering | MultipleScatteringe- |
| positron | Ionization | StandardModele- |
|  | Bremsstrahlung | StandardModele- |
|  | Multiple Scattering | MultipleScatteringe- |
|  | Positron Annihilation |  |

Regarding system matrix with respect to the second example embodiment, the MC emission data were recorded in list-mode format using the ROOT object oriented data analysis framework and were later binned into a sinogram format. Each sinogram included a 400 (radial bins)×336 (angular bins) array. The total number of detector rings for the mCT was 55 (52 physical rings and 3 virtual rings between the 4 detector block rings), as per the original mCT system matrix. For the Ex-mCT, each detector block ring encompassed 7 sparse LSO rings interleaved with six 4 mm physical gaps in the axial direction. The gaps were treated as virtual detector rings, thus resulting in a total of 111 detector (physical+virtual) rings in the system matrix. A maximum ring difference (MRD) of 49 was used for the mCT (as per manufacturer recommendation). A MRD of 105 was selected for the Ex-mCT such that exactly the five most oblique 2D sinogram planes were excluded as it was in the case of the mCT system matrix. All PET simulations were carried out with no TOF information.

Regarding normalization correction, a 70 cm long, 70 cm inner diameter, and 70.1 cm outer diameter annulus phantom was simulated with water equivalent density and 1.8 MBq of $^{18}$F, using the mCT, and then the Ex-mCT MC models. A total of 600 million coincidence events were acquired in each case (see, e.g., Pépin A, Stute S, Jan S and Comtat C 2011 IEEE Nuclear Science Symposium Conference Record, 23-29, October 2011 vol. series pp 4196-200). The system normalization was performed using a component-based approach (as described by Casey M, Gadagkar H and Newport D 1996 A component based method for normalization in volume PET). The following four normalization components were calculated for each of the mCT and the Ex-mCT: geometric effect, crystal interference, crystal efficiency, and the axial effect. The inverse of the product of the four components was then calculated for each detector pair and then binned into the normalization factors sinogram of each system. Normalization correction was finally applied within the 3D-OSEM reconstruction.

The system spatial resolution, sensitivity, and image quality were evaluated for both the mCT (gold standard) and Ex-mCT according to the NEMA NU 2-2007 guidelines to evaluate system performance. Regarding spatial resolution, $^{18}$F point sources (1 mm in diameter and 8 MBq activity), each enclosed by glass spherical shells (1 mm internal diameter and 0.5 mm thick), were simulated at the following positions: (0, 1 cm), (0, 10 cm) and (10 cm, 0) at the center, and again at the $¼^{th}$ axial FOV for the mCT and the Ex-mCT models respectively. Three independent 20 sec acquisitions were simulated for each point source, and then reconstructed using the FBP-3D reprojection analytic algorithm (FBP3DRP) algorithm from STIR, with a 400×400 image matrix (1×1 mm² pixel size, 2 mm slice thickness) and without normalization correction. Line profiles along the x, y and z directions were drawn through the highest intensity pixel for each point source, using ImageJ, and then the respective full width at half maxima (FWHM) were measured. The system transaxial and axial spatial resolutions were defined as per NEMA NU 2-2007 (2007).

Regarding sensitivity of the second example embodiment, a 70 cm polyethylene tubing shell (1 mm diameter and 1 mm wall thickness) was simulated with 4 MBq of $^{18}$F in water equivalent density. The line source was simulated along the scanner tomographic axis, at the center of the transaxial field of view, and again at 10 cm off-center. PET data were acquired for 100 seconds at each source position, first for the mCT, and then for the Ex-mCT. The axial sensitivity profile for each line source position was measured by summing the total number of true coincidences per slice using single slice rebinning, normalized by source activity and total scan time. The system sensitivity was then calculated by integrating the axial sensitivity profiles of each position across all transaxial slices (109 for the mCT and 219 for the Ex-mCT) and then averaging over the two positions.

Regarding image quality of the second example embodiment, modified version of the NEMA IEC (M-IEC) phantom was simulated to evaluate each of the mCT and Ex-mCT image quality performances. The M-IEC phantom consisted of a plastic cylinder of 14.7 cm radius and 21.4 cm height filled with an aqueous solution of water equivalent density and 5.3 kBq/ml of $^{18}$F. Six plastic equivalent spheres of 1 mm thickness and 10, 13, 17, 22, 28, and 37 mm internal diameters, respectively, were simulated inside the phantom's cylindrical compartment with their centers confound within the same transaxial plane, at 7 cm distance from the top of the phantom (similar to the NEMA IEC phantom). The spheres were filled with an aqueous solution of water equivalent density and 21.2 kBq/ml $^{18}$F, resulting in a target-to-background ratio (TBR) of 4:1.

1, 3, 6 and 9 min acquisitions of the M-IEC phantom were simulated for each of the mCT and Ex-mCT models, respectively. The corresponding PET images, of 109 slices for the mCT and 219 slices for the Ex-mCT, were reconstructed using the 3D-OSEM image reconstruction algorithm (1 iteration, 24 subsets, image matrix size of 245×245, pixel size of 2.699×2.699 mm$^2$, slice thickness of 2 mm, 4 mm FWHM Gaussian post filter) with randoms, attenuation and normalization correction as implemented in STIR excluding scatters. The number of iterations was chosen for the maximum signal-to-noise ratio of the 37 mm sphere for both mCT and Ex-mCT and the 24 subsets were used as a multiple of the image views number as recommended by STIR. Percentage contrast recovery (CR) and background variability (BV) were calculated for each sphere i as follows:

$$CR_i = \frac{S_i / \overline{Bk}_{i,60}}{S_{i,Act} / Bk_{i,Act}} \times 100 \quad (3)$$

$$BV_i = \frac{\sigma_{i,Bk}}{\overline{Bk}_{i,60}} \times 100 \quad (4)$$

where $S_i$ is the mean number of counts inside a region of interest (ROI) drawn at the center of, and with the same diameter as, sphere i; $\overline{Bk}_{60}$ is the average of the mean number of counts inside 60 background ROIs with diameter equal to that of sphere i, 12 of which drawn on each of the transaxial slices at 0 mm, ±2 mm, ±4 mm from the spheres centers plane; $S_{i,Act}/Bk_{i,Act}$ is the theoretical TBR (4:1), and $\sigma_{i,Bk}$ is the standard deviation of the mean counts inside the 60 background ROIs. Three independent 9 min PET acquisitions were performed for both scanner configurations to calculate the standard error in CR and BV metrics.

Regarding axial noise uniformity of the second example embodiment, the NEMA M-IEC phantom, without the hot spheres inserts, was simulated with a uniform background $^{18}$F activity distribution of 5.3 kBq/ml to study the noise characteristics of the Ex-mCT model. MC simulations of 9 min PET acquisitions were performed for the mCT (gold standard), and the Ex-mCT models respectively. The corresponding PET images were reconstructed with 3D-OSEM using the same parameters as for the image quality study. A 10 cm diameter ROI was drawn at the center of the cylinder in each of 104 transaxial slices covering the M-IEC phantom. The noise level in each transaxial image was defined as:

$$N_j = \frac{\sigma_{j,B}}{B_j} \quad (5)$$

where $N_j$ is the noise level in slice j, and $\sigma_{j,B}$ and $\overline{B}_j$ are the standard deviation and mean counts within the ROI in slice j respectively.

Regarding spatial resolution of the second example embodiment, the Ex-mCT spatial resolution was evaluated at 1 cm and 10 cm off-axis, and then compared to that of the mCT (Table 2). Less than 5% difference in transaxial spatial resolution was shown between the mCT and Ex-mCT. Axially, ~17% degradation in Ex-mCT spatial resolution was observed at 1 cm off-center. Simulating for 20 sec, 60 sec and 100 sec did not affect the spatial resolution in both configurations and we did not see any significant change related to the number of detected counts.

TABLE 1

Spatial Resolution for the mCT and Ex-mCT. The mean values from three different reconstructed images and their standard deviation are listed in this table.

|  | mCT | Ex-mCT |
|---|---|---|
| At 1 cm |  |  |
| Transverse | 4.11 ± 0.09 mm | 4.19 ± 0.01 mm |
| Axial | 4.49 ± 0.03 mm | 5.27 ± 0.03 mm |
| At 10 cm |  |  |
| Transverse Radial | 4.47 ± 0.03 mm | 4.58 ± 0.02 mm |
| Transverse Tangential | 4.69 ± 0.01 mm | 4.48 ± 0.02 mm |
| Axial Resolution | 5.42 ± 0.00 mm | 5.73 ± 0.05 mm |

Regarding sensitivity of the second example embodiment, the axial sensitivity profiles at 0 cm for the mCT and Ex-mCT are displayed in FIGS. 2(a), and 2(b) respectively. Similar profiles were observed at 10 cm off-center for both models. The Ex-mCT sensitivity profile shows interleaved gaps, which are the result of the sparse detector rings configuration. The Ex-mCT exhibited a 13% increase in sensitivity, compared to the mCT, which is attributed to the four additional physical detector rings (56 vs 52 rings for the mCT), as it was explained earlier. The system sensitivities at the center of the transaxial FOV and 10 cm off-center for both scanners are summarized in Table 3.

TABLE 2

Average sensitivity at the center and 10 cm positions for the mCT and the Ex-mCT The mean values from three different acquistions and their standard deviation are listed in this table.

| Sensitivity (cps/kBq) | mCT | Ex-mCT |
|---|---|---|
| Center | 9.10 ± 0.10 | 10.39 ± 0.19 |
| 10 cm | 9.18 ± 0.09 | 10.47 ± 0.19 |

Figure 12:
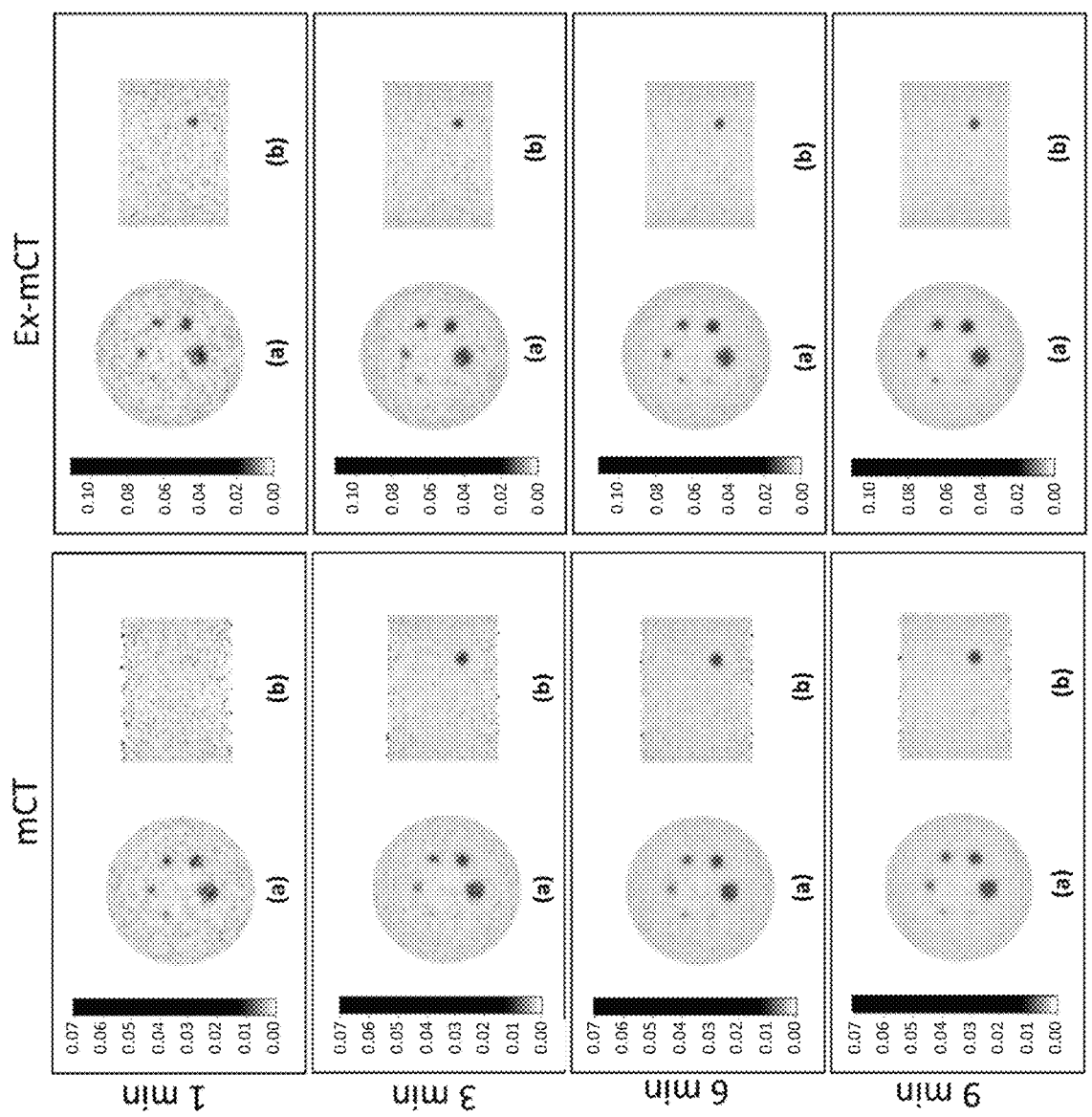
FIG. 12 depicts Ordered Subsets Expectation Maximization (OSEM) reconstructed images of the image quality phantom for 1, 3, 6, and 9 minute durations for the mCT (left column) and Ex-mCT (right column), according to potential embodiments. The transverse plane "(a)" (on the left side in each of the left and right columns) through the axial center of the spheres and the coronal view "(b)" (on the right side of each of the left and right columns) through the center of the smallest sphere (10 mm diameter) are displayed for each time duration and scanner configuration. All images are normalized to scan time and to each other. All images were reconstructed with 1 iteration, 24 subsets, 245×245 images matrix, 2.699×2.699 mm2 pixel size, 2 mm slice thickness, 4 mm FWHM Gaussian post filter.
Figure 13B:
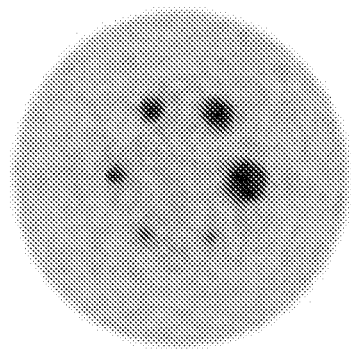
FIGS. 13A-13D depict reconstructed images of image quality phantom with OSEM, according to potential embodiments. The top images FIGS. 13A, 13C display the transverse plane through the axial center of the spheres and the bottom images
Figure 13D:
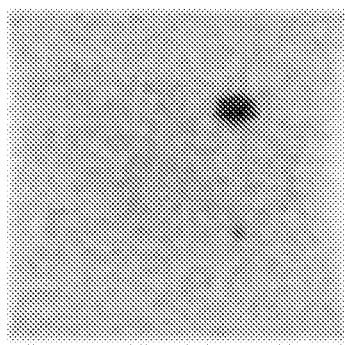
Figure 13A:
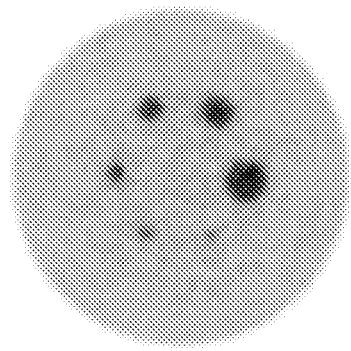
Figure 13C:
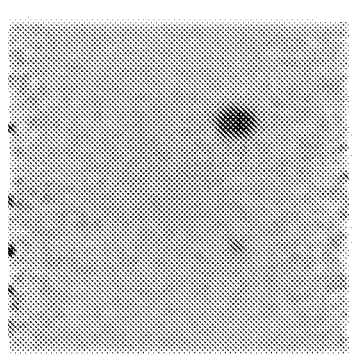

Regarding image quality, FIG. 12 (see "(a)") displays the transaxial images through the centers of the 6 spheres of the NEMA M-IEC phantom acquired using the mCT and Ex-mCT MC models respectively for 1, 3, 6 and 9 min acquisitions. The corresponding coronal slices through the center of the 10 mm and 28 mm diameter spheres are also displayed at FIG. 12 (see "(b)"). No image artifacts were observed in all cases. The 1 min images are noisy in the mCT and the Ex-mCT and the images become clearer with increased acquisition duration. The smallest 10 mm diameter sphere starts to get detectable after 6 min and at 9 min all 6 spheres were visually detectable. The images with 1 iteration and 24 subsets were chosen since they showed highest SNR with respect to the 37 mm diameter sphere in mCT and Ex-mCT models. Quantitative analysis were performed on the 9 min acquisition images similar to the work done by Jakoby et. al. where they scanned for a total of 10 min as per NEMA guidelines. Less than 3% difference in percent CR between the two scanners configurations was demonstrated. Visual inspection of the two image sets showed a slight increase in noise level in the Ex-mCT images compared to those of the mCT. This is tabulated in the background variability measurements summarized in Table 4. However, the differences in background variabilities between the two scanner models for each of the six spheres were statistically insignificant (two-tailed t-test showed p>0.05).

TABLE 4

Percentage contrast recovery and background variability of the hot
spheres in reconstructed PET images for mCT and Ex-mCT configurations.

| Sphere diameter | 10 mm | 13 mm | 17 mm | 22 mm | 28 mm | 37 mm |
|---|---|---|---|---|---|---|
| % CR | | | | | | |
| mCT | 42.15 ± 4.24 | 47.86 ± 0.66 | 56.83 ± 2.36 | 61.42 ± 0.99 | 66.12 ± 1.69 | 69.68 ± 1.04 |
| Ex-mCT | 41.48 ± 4.76 | 46.62 ± 2.38 | 57.45 ± 1.30 | 61.50 ± 0.72 | 67.5 ± 0.72 | 69.89 ± 1.59 |
| % BV | | | | | | |
| mCT | 4.78 ± 0.62 | 4.05 ± 0.67 | 3.27 ± 0.61 | 2.62 ± 0.63 | 2.19 ± 0.64 | 1.84 ± 0.55 |
| Ex-mCT | 5.92 ± 0.35 | 5.15 ± 0.21 | 4.20 ± 0.05 | 3.39 ± 0.19 | 2.82 ± 0.28 | 2.22 ± 0.21 |

CR: contrast recovery. BV: background variability. The mean values from three different reconstructed images and their standard deviation are listed in this table.

Figure 14:
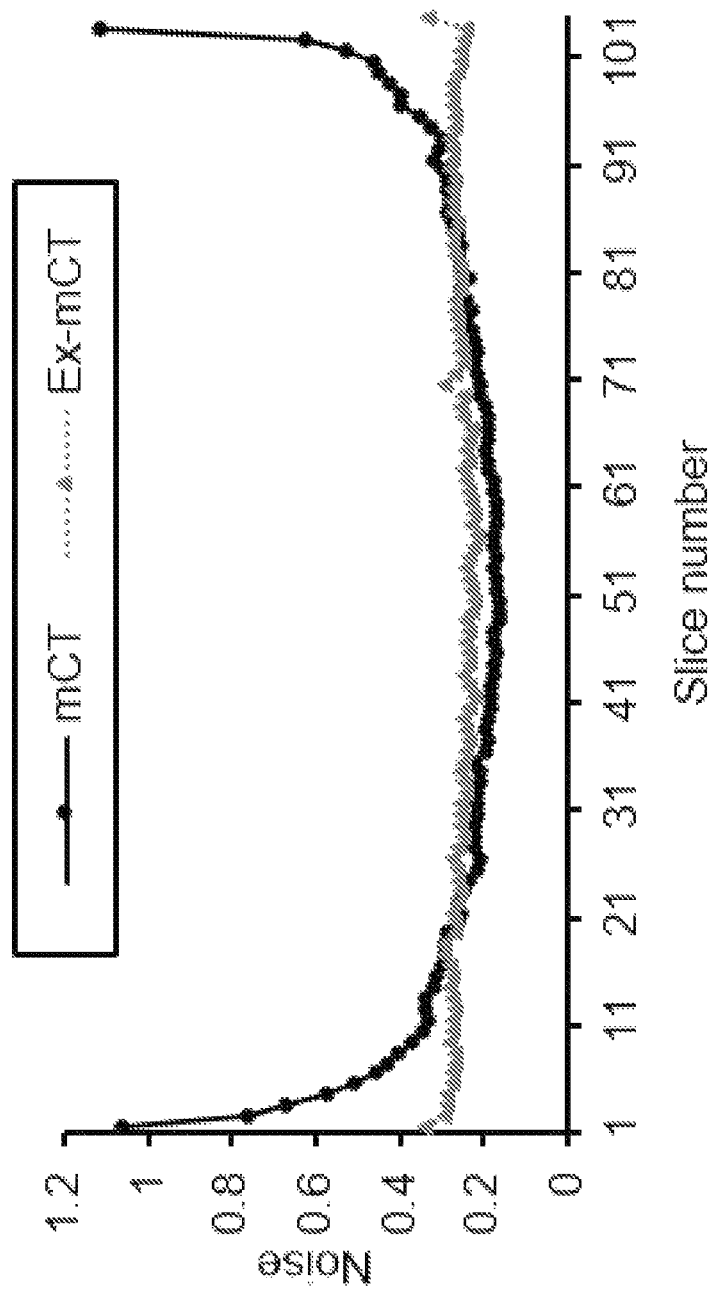
FIG. 14 depicts noise level per slice in a uniform cylinder for 9-minute acquisitions in the mCT and the Ex-mCT configurations, according to potential embodiments.

Regarding axial noise uniformity, FIG. 14 depicts noise levels versus the transaxial slice number, Nj, for the 104 most-central transverse slices corresponding to the location of the uniform cylinder in both scanner scans. This set of slices also denotes the overlapping AFOV section between the two scans. The Ex-mCT exhibited 36% higher noise levels, compared to mCT, yet, relatively uniform across all 104 slices. However, about three-fold increase in the mCT noise levels, compared to those at the center of the AFOV, was observed at the two axial edges of the cylindrical phantom, which corresponded to the edges of the mCT axial FOV.

Conventional PET scanners are limited by their short AFOV, typically less than 26 cm. A longer AFOV shall extend PET research scope in cancer, cardiology, and neurology, and in particular, simultaneous multi-organ imaging (e.g. heart-brain) and kinetic modeling. In the second example embodiment, a PET prototype, Ex-mCT, with extended AFOV and a sparse rings configuration, and that was based on the Siemens Biograph™ mCT scanner geometry, was validated. Ex-mCT allowed almost the doubling of the mCT original AFOV while maintaining a similar number of LSO elements.

To address increased parallax effect, the acceptance angle was increased from ±150 (mCT) to ±28° (Ex-mCT). In a sparse detector rings configuration, such in the case of the Ex-mCT, parallax effect may be enhanced in particular for small acceptance angles, due to the increased apparent crystal size; gamma photons penetrating through the physical gaps will hit the side (20 mm long) of a crystal. This can be reduced by incorporating depth-of-interaction (DOI) correction techniques (see, e.g., Schmall J P, Karp J S, Werner M and Surti S 2016, Parallax error in long-axial field-of-view PET scanners—a simulation study, *Phys Med Biol* 61 5443-55).

Figure 11A:
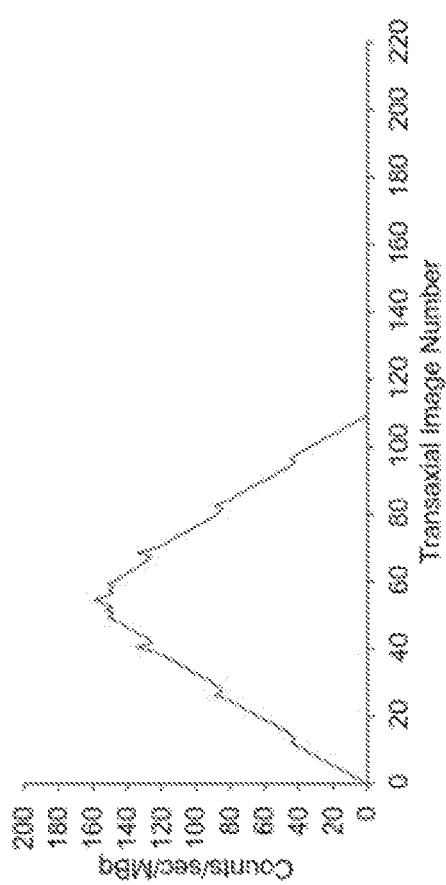
FIGS. 11A and 11B depict axial sensitivity profiles at the center of the transaxial field-of-view for the mCT (FIG. 11A) and ex-PET (FIG. 11B) systems, according to potential embodiments.
Figure 11B:
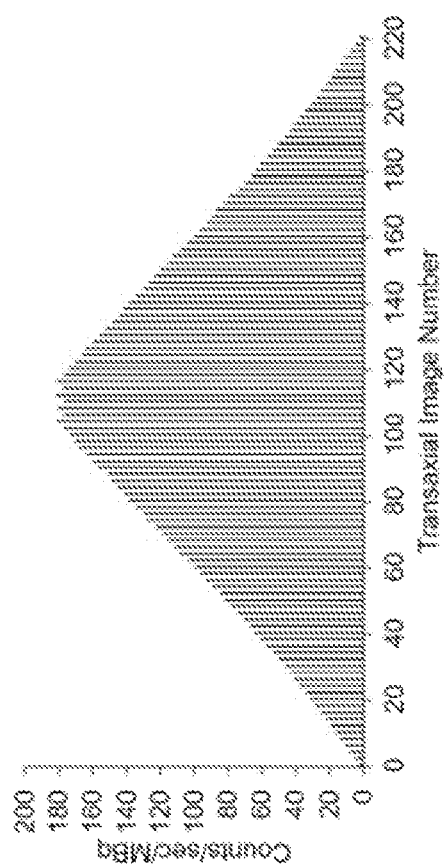

In the Ex-mCT configuration, the original mCT block dimensions was preserved when incorporating the axial physical gaps in between the LSO crystals (see FIGS. 11A and 11B) with respect to the second example embodiment. This resulted in four additional detector rings compared to the mCT (56 vs 52), which yielded a 13% increase in the Ex-mCT system sensitivity compared to that of the mCT (Table 3). However, in projection space, planes corresponding to LORs between physical and virtual, and, virtual and virtual, detector pairs exhibited zero counts. This is demonstrated by the lack of counts in specific transaxial slices of the axial sensitivity profile (FIG. 11B). In image space, 3D iterative reconstruction together with the adequate normalization correction allowed to partially compensate for the missing spatial information. The accuracy in recovering the missing counts was assessed using the NEMA M-IEC phantom (FIG. 12). In both mCT and Ex-mCT models, all six spheres were visually detectable, and a maximum difference of less than 3% in contrast recovery was measured between the two scanner models for all six spheres. The increased AFOV of the Ex-mCT, while maintaining equivalent system sensitivity as the mCT, resulted in reduced sensitivity per transaxial slice. This was demonstrated by an increase in the background variability, BV, in the NEMA M-IEC images, ranging between ~20% (37 mm diameter ROI) and ~30% (22 mm diameter ROI), compared to that of the mCT (table 4). However, the reduced standard errors in BV of the M-IEC phantom images as well as the relatively flat noise levels in the cylindrical phantom images (FIG. 14) demonstrates that the Ex-mCT exhibits better noise uniformity compared to the mCT.

This shall have major impact on the diagnostic image quality of clinical PET images of single organs such as the brain, liver, and heart, compared to images acquired with the mCT. The longer AFOV of Ext-mCT enables simultaneous PET imaging of distant organs, thus setting the stage for new research pathways involving multi-organ interactions such in the case of brain and heart, which would not been possible otherwise.

In various embodiments, the spacing between parallel detector rings is adjustable. For example, gaps between rings may be adjustable between a compact configuration, in which the detector rings are in contact or otherwise relatively closer to each other, and an expanded configuration (or sparse ring configuration), in which two or more detector rings have been moved apart from each other to varying degrees. The detector rings, or scanner in which the detector rings are incorporated, may include any drive mechanism capable of implementing a change in gaps/spacing between detector rings. The drive mechanism may comprise an expander, which may be coupled to a controller capable of sending control signals to the expander to adjust the spaces between detector rings. In various embodiments, the expander may, alternatively or additionally, use motors, gears, wheels, axels, springs, hydraulics, etc. In certain embodiments, the drive mechanism may include electromagnetic components which repel and/or attract detector rings to varying degrees, as desired, based on magnitudes of electrical current (adjustable via, e.g., the controller of the drive mechanism) applied thereto.

Figure 15:
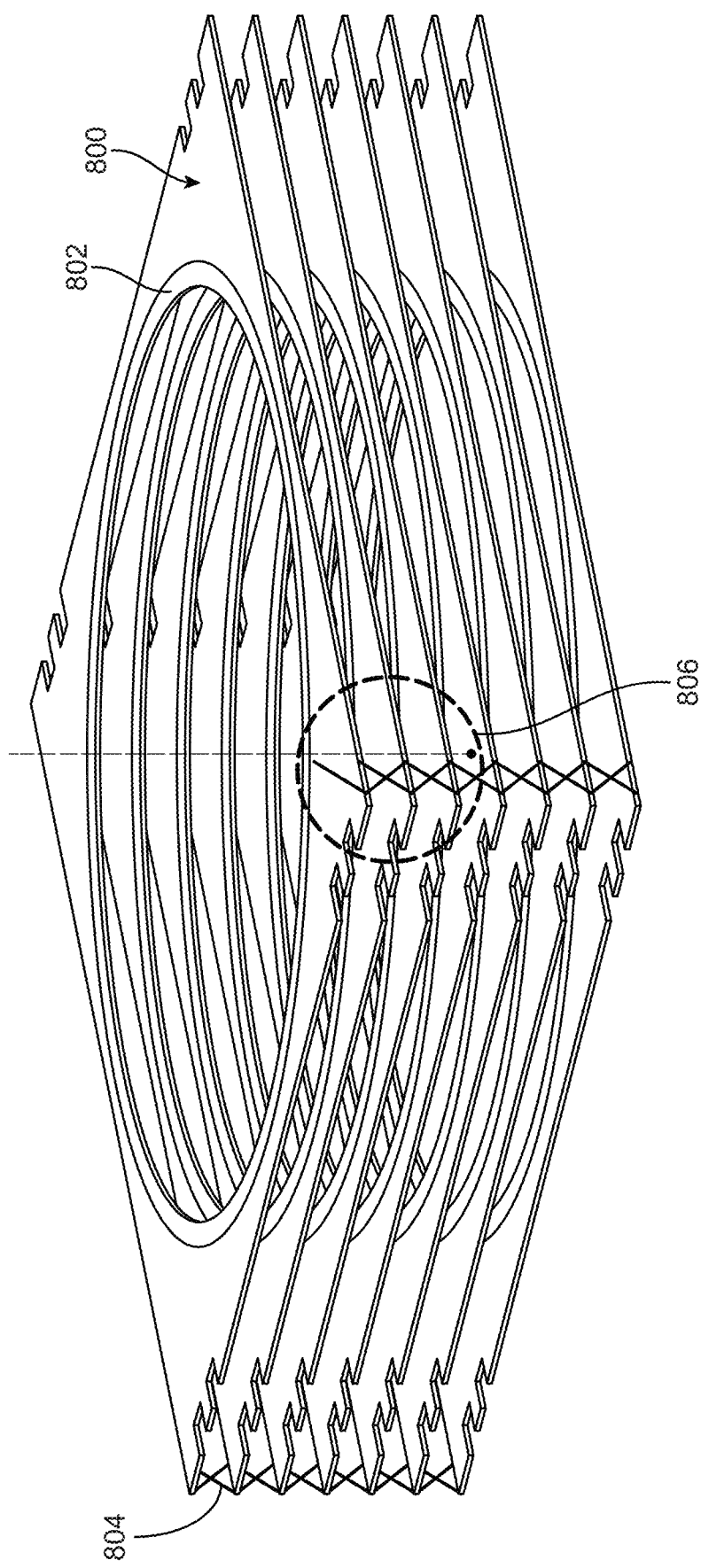
FIG. 15 depicts a set of parallel detector plates for an example sparse ring PET scanner, according to potential embodiments.

Referring to FIG. 15, a sparse ring PET detector can include a plurality of plates 800. Each of the plates 800 can include a ring 802. The ring 802 can be a crystal-based PET detector ring. The plates 800 (and rings 802) can be driven toward one another and into a compact or retracted configuration by an expander that comprises a lift mechanism 804. In some implementations, in the retracted configuration each of the plates 800 can be flush against one another. In some implementations, the sparse ring PET detector can include spacers that can cause a predetermine gap between each of the plates 800 and rings 802 in the retracted configuration. The lift mechanism 804 can drive the plates 800 and rings 802 away from one another and into the extended or sparse configuration. The insert 806 is illustrated in FIG. 16 and provides an enlarged view of the lift mechanism 804.

Figure 16:
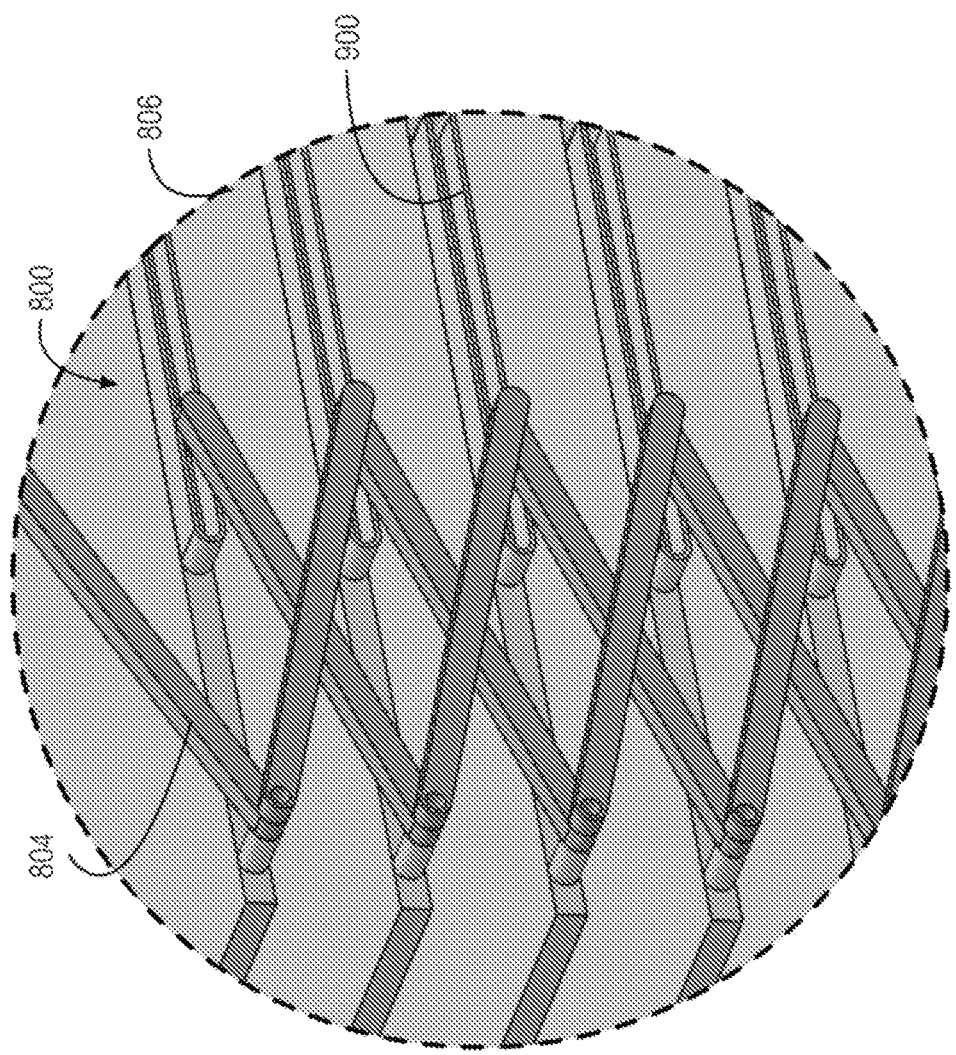
FIG. 16 illustrates an example lift mechanism for the detector plates of FIG. 15, according to potential embodiments.

FIG. 16 illustrates the example lift mechanism 804. The lift mechanism 804 can drive the plates 800 and rings 802 toward or away from one another. In some implementations, the lift mechanism 804 can be configured as a scissors lift mechanism. The lift mechanism 804 can be controlled by one or more stepper motors. The scissor lift mechanism can include a plurality of pins. For each of the plates 800, a first pin can be coupled to a fix position on the plate 800. The second pin can be position in a track 900 that enables the pin to slide along the length of the plate 800 as the lift mechanism 804 extends or retracts.

In various embodiments, with respect to detector rings, each PET detector ring may encompass any number of detector elements in the axial direction. The axial number of detector elements may be same across all detector rings, or variable with different rings having different number of detector elements axially.

In various embodiments, with respect to detector element size, the single detector element dimension shall be same or variable across the whole PET system. In the case of variable detector element dimensions, different detector rings may have different detector elements sizes.

In various embodiments, with respect to spacing among the detector rings, the spacing among the detector rings may be uniform, that is, the same in between each two consecutive rings, or position dependent, thus different axial gap sizes exist at different position along the axial FOV.

In various embodiments, with respect to detectors orientation, the detector elements at different detector rings shall have same or different orientations to optimize system sensitivity and/or resolution.

In various embodiments, with respect to on-the-fly dynamic axial FOV, the axial FOV and/or the spacing between the detector rings may be optimized before, after, or within the data acquisition of a PET bed position acquired during static or dynamic modes.

In various embodiments, with respect to transaxial sparse detectors, detector elements in each detector ring may be spaced out uniformly or non-uniformly in the transaxial plane.

In various embodiments, with respect to data interpolation, the PET scanner sparse configuration with small uniform axial gaps every other detector ring may be accompanied by an axial projection interpolation method to infer the missing measurements in the gaps and address any noise enhancement expected from the reconstruction of axially sparse PET data.

In various embodiments, with respect to system normalization, a component-based normalization method for the sparse and interpolated PET data may be implemented to properly account for the sensitivity of the scanner at gaps before and/or after interpolation, which may be later used within the 3D PET image reconstruction to produce image quality comparable to that of compact ring PET scanner configurations but at half the (or otherwise lower) manufacturing cost.

In various embodiments, with respect to continuous bed motion, the PET scanner sparse configurations (e.g., with relatively larger gaps equivalent to the size of block detector rings and uniformly distributed every other block ring) support PET acquisitions during continuous bed motion (CBM). The CBM acquisition of sparse PET data with axially sparse configuration eliminates (or otherwise minimizes or considerably reduces) any gaps in the axial sensitivity profile of the sparse configuration thereby allowing for axially smooth changes in sensitivity performance along the entire axial FOV similar to the sensitivity of current state-of-the-art clinical PET systems with compact ring configurations.

In various embodiments, with respect to system sensitivity, a sparse configuration may attain the same overall sensitivity along an axial FOV that is twice as large as the axial FOV of compact ring configurations of the same number of rings and thus of the same manufacturing cost.

In various embodiments, with respect to improvement in noise uniformity, the longer axial FOV and the smooth axial sensitivity profile attained, regardless of the size of the uniformly distributed axial gaps, allow for less variable noise levels in the center of the axial FOV of the sparse versus the compact ring configurations. This feature of the sparse block ring configuration is particularly beneficial for single organ imaging (e.g., brain or heart), as well as large organs or lesions distribution extending beyond the conventional axial FOV of compact ring configurations.

In various embodiments, with respect to system compatibility, the PET sparse configuration is compatible with any number of detector rings and gantry diameter, including "Total-Body PET".

In various embodiments, with respect to compatibility with software/hardware technologies, 3D PET normalization and reconstruction of axially or transaxially sparse PET data is compatible with time-of-flight PET, list-mode and sinogram-based analytical (e.g., filtered back projection, FBP) and statistical (e.g., maximum likelihood expectation-maximization, MLEM, with or without ordered subsets or maximum-a-posteriori, MAP, priors including those imposing data sparsity constraints, point spread function modeling) PET image reconstruction algorithms. Moreover, the image reconstruction, projection-based axial interpolation and continuous bed motion technologies are all compatible with the parallel utilization of machine learning, deep learning or other artificial intelligence methods involving the supervised or unsupervised training of neural networks to restore the image quality and eliminate noise due to the presence of axial or transaxial gaps.

In various embodiments, with respect to pre-clinical PET scanner, PET imaging with sparse detector ring configuration may be incorporated for pre-clinical PET imaging.

In various embodiments, with respect to dynamic axial FOV for different animal length, the PET scanner axial FOV may be extended using a sparse rings configuration to allow imaging of large animals, or contracted for small animals settings.

In various embodiments, with respect to dynamic PET gantry diameter for different animal sizes, the transaxial PET FOV may be extended or contracted to account for large or small animals diameters, respectively. For this, the detector structures in each ring may be translated radially to optimize the PET gantry diameter. The PET ring diameter may be dynamic by translating the individual PET detector structures radially. Radial translations may be achievable via mechanical systems similar to the systems capable of achieving and/or dynamically changing axial translations, with similar mechanical components.

In various embodiments, with respect to continuous PET gantry rotation, in the case of sparse detector elements (or detector modules) in the PET transaxial plane, the PET gantry may be rotated to compensate for the missing data information.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations (used interchangeably with embodiments), it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Similarly, a reference to "at least one of 'A' or 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A positron emission tomography (PET) imaging system comprising:
    a controller having a processor and a memory with instructions executable by the processor to control scanning of subjects;
    a PET scanner having a set of detector structures sharing a common axis, each detector structure having one or more radiation detectors, wherein each detector structure has a corresponding axial width, and wherein the detector structures are spaced apart from each other along the axis to define gaps between detector structures in the set of detector structures such that an axial field-of-view (FOV) of the PET imaging system is greater than a sum of the corresponding axial widths of the detector structures; and
    a scanner driver configured to adjust gaps between detector structures in the set of detector structures so as to adjust the axial FOV of the PET imaging system;
    wherein the controller is configured to perform a first scan using the PET scanner with a first set of gaps between detector structures, determine a second set of gaps based on the first scan, control the scanner driver to adjust gaps between detector structures to correspond with the second set of gaps, and perform a second scan following adjustment of gaps.

2. The system of claim 1, wherein each detector structure in the PET scanner comprises a same number of radiation detectors in an axial direction.

3. The system of claim 1, wherein a first detector structure of the set of detector structures in the PET scanner comprises a first number of radiation detectors in an axial direction and a second detector structure of the set of detector structures in the PET scanner comprises a second number of radiation detectors in the axial direction.

4. The system of claim 1, wherein each radiation detector in the PET scanner has a same set of dimensions.

5. The system of claim 1, wherein a first subset of radiation detectors in the PET scanner have a first set of dimensions and a second subset of radiation detectors in the PET scanner have a second set of dimensions different from the first set of dimensions, wherein each radiation detector in the second subset is different from any of the radiation detectors in the first subset.

6. The system of claim 1, wherein gaps between detector structures are uniform in the PET scanner.

7. The system of claim 1, wherein gaps between detector structures are variable in the PET scanner.

8. The system of claim 7, wherein gaps between detector structures are position-dependent such that axial gaps differ at different positions in the set of detector structures.

9. The system of claim 1, wherein each radiation detector in the PET scanner has a same orientation.

10. The system of claim 1, wherein orientations of radiation detectors in the PET scanner vary such that a first subset of radiation detectors in the PET scanner have a first orientation and a second subset of radiation detectors in the PET scanner have a second orientation different from the first orientation, wherein each radiation detector in the second subset is different from any of the radiation detectors in the first subset.

11. The system of claim 1, wherein the controller is configured to determine spacing between detector structures based on a criterion, control the scanner driver to adjust gaps between detectors structures to correspond with the determined spacing, and perform a scan with the PET scanner following adjustment of gaps.

12. The system of claim 1, wherein the controller is configured to perform a scan with the PET scanner and use the scanner driver to dynamically adjust gaps between detector structures during the scan.

13. The system of claim 1, wherein the controller is configured to control the scanner driver to adjust gaps based on a size of a subject to be scanned.

14. The system of claim 1, wherein radiation detectors in each detector structure are spaced uniformly in a transaxial plane.

15. The system of claim 1, wherein radiation detectors in each detector structure are spaced non-uniformly in a transaxial plane.

16. The system of claim 1, wherein the controller is configured to apply an axial projection interpolation model to infer measurements missing due to gaps between detector structures.

17. The system of claim 1, wherein the controller is configured to apply a component-based normalization model to PET scan data before three-dimensional PET image reconstruction.

18. The system of claim 1, wherein the gaps are uniformly distributed and wherein the gaps separate detector structures by distances about equal to axial widths of the detector structures.

19. The system of claim 1, wherein the controller is configured to scan subjects via continuous bed motion (CBM) acquisition of PET data to compensate for data loss due to gaps between detector structures.

20. The system of claim 1, wherein the axial FOV of the PET imaging system is larger than a compact-structure configuration in which there are no gaps between detector structures.

21. The system of claim 20, wherein the axial FOV is more than twice as large as the compact-structure configuration.

22. The system of claim 1, wherein the controller is configured to rotate a gantry during scanning to compensate for data missing due to gaps between detector structures.

23. The system of claim 1, wherein the controller is configured to apply at least one of sparse data reconstruction models, machine learning models, deep learning models, or other artificial intelligence models to compensate for loss of counts due to gaps between detector structures.

24. A method of performing positron emission tomography (PET) scanning of a subject using a PET imaging system having a PET scanner with a set of detector structures that share a common axis and that are axially spaced apart from each other so as to define gaps between detector structures, each detector structure having one or more radiation detectors, the method comprising:
performing, via a controller of the PET imaging system, a first scan of a subject to capture a first PET dataset with a first axial field-of-view (FOV), wherein the set of detector structures are separated from each other by a first set of gaps between detector structures;
determining, via the controller and based on the first PET dataset, a second set of gaps between detector structures corresponding to a second axial FOV different from the first axial FOV;
applying, via the controller, the second set of gaps to the set of detector structures to change distances between detector structures; and
performing, via the controller, a second scan of the subject to capture a second PET dataset with a second axial FOV.

25. The method of claim 24, further comprising applying, via the controller, an axial projection interpolation model to infer measurements missing due to gaps between detector structures.

26. The method of claim 24, further comprising at least one of continuous bed motion (CBM) or gantry rotation, via the controller, during scanning to compensate for data missing due to gaps between detector structures.

* * * * *